(12) United States Patent
Walsh et al.

(10) Patent No.: US 11,464,647 B2
(45) Date of Patent: Oct. 11, 2022

(54) DEVICES FOR BONE INTEGRATION

(71) Applicant: NEWSOUTH INNOVATIONS PTY LIMITED, Sydney (AU)

(72) Inventors: William Robert Walsh, New South Wales (AU); Matthew Henry Pelletier, New South Wales (AU)

(73) Assignee: NEWSOUTH INNOVATIONS PTY LIMITED, Sydney (AU)

(*) Notice: Subject to any disclaimer, the term of this patent is extended or adjusted under 35 U.S.C. 154(b) by 440 days.

(21) Appl. No.: 16/065,921

(22) PCT Filed: Dec. 21, 2016

(86) PCT No.: PCT/AU2016/051263
§ 371 (c)(1),
(2) Date: Jun. 25, 2018

(87) PCT Pub. No.: WO2017/106912
PCT Pub. Date: Jun. 29, 2017

(65) Prior Publication Data
US 2019/0046331 A1      Feb. 14, 2019

(30) Foreign Application Priority Data
Dec. 24, 2015   (AU) ................................ 2015905393

(51) Int. Cl.
*A61F 2/44*   (2006.01)
*A61F 2/30*   (2006.01)

(52) U.S. Cl.
CPC ........ *A61F 2/4455* (2013.01); *A61F 2/30767* (2013.01); *A61F 2002/30014* (2013.01); *A61F 2002/3093* (2013.01); *A61F 2002/30593* (2013.01); *A61F 2002/30733* (2013.01); *A61F 2310/00359* (2013.01)

(58) Field of Classification Search
CPC .............................. A61F 2/4455; A61F 2/447
See application file for complete search history.

(56) References Cited

U.S. PATENT DOCUMENTS

| | | | |
|---|---|---|---|
| 8,100,972 B1 | 1/2012 | Bruffey et al. | |
| 10,299,938 B1 * | 5/2019 | Ehteshami | .............. A61F 2/447 |
| 2010/0152856 A1 | 6/2010 | Overes et al. | |

(Continued)

FOREIGN PATENT DOCUMENTS

| | | |
|---|---|---|
| EP | 1430857 A1 | 6/2004 |
| WO | 9532673 A1 | 12/1995 |

(Continued)

OTHER PUBLICATIONS

International Search Report with Written Opinion for Application No. PCT/AU2016/051263 dated Feb. 17, 2017 (20 pages).

(Continued)

*Primary Examiner* — Nicholas W Woodall
(74) *Attorney, Agent, or Firm* — Michael Best & Friedrich LLP

(57) ABSTRACT

A device adapted to be positioned between two bone regions, the device comprising at least one wall defining at least one interior cavity, and, a load arrangement extending from the wall and comprising at least one interacting feature configured to load material positioned within the cavity by interacting with either a second interacting feature or the wall.

23 Claims, 25 Drawing Sheets

(56) References Cited

U.S. PATENT DOCUMENTS

| | | | |
|---|---|---|---|
| 2012/0065733 A1 | 3/2012 | Wieder | |
| 2012/0303127 A1 | 11/2012 | Ullrich, Jr. et al. | |
| 2013/0018472 A1 | 1/2013 | Yue | |
| 2013/0090735 A1 | 4/2013 | Mermuys et al. | |
| 2013/0116793 A1* | 5/2013 | Kloss | A61F 2/442 623/17.16 |
| 2014/0288650 A1* | 9/2014 | Hunt | A61F 2/30907 623/16.11 |
| 2017/0333205 A1* | 11/2017 | Joly | A61F 2/4455 |
| 2019/0000636 A1* | 1/2019 | Kim | A61F 2/4455 |
| 2019/0099274 A1* | 4/2019 | Duarte | A61F 2/30771 |
| 2019/0183651 A1* | 6/2019 | Schlachter | A61F 2/28 |
| 2019/0274841 A1* | 9/2019 | Hawkes | A61F 2/442 |
| 2019/0343645 A1* | 11/2019 | Miccio | A61F 2/30771 |

FOREIGN PATENT DOCUMENTS

| | | | |
|---|---|---|---|
| WO | 2009025884 A2 | 2/2009 |
| WO | 2012010327 A1 | 1/2012 |
| WO | 2014159739 A1 | 10/2014 |
| WO | 2016029254 A1 | 3/2016 |

OTHER PUBLICATIONS

European Patent Office Extended Search Report for Application No. 16877001.4 dated Jan. 30, 2020 (10 pages).

* cited by examiner

A: Control LB1
Total Deformation
Type: Total Deformation
Unit: mm
Time: 1

2.01 Max
1.79
1.56
1.34
1.12
0.893
0.67
0.446
0.223
0 Min

A: Control LB1
Total Deformation
Type: Total Deformation
Unit: mm
Time: 1

2.01 Max
1.79
1.56
1.34
1.12
0.893
0.67
0.446
0.223
0 Min

A: Control LB1
Equivalent Stress 4
Type: Equivalent (von-Mises) Stress
Unit: MPa
Time: 1

11.5 Max
2
1.75
1.5
1.25
1
0.751
0.502
0.252
0.00212 Min

C: Control 9 LB1
Total Deformation
Type: Total Deformation
Unit: mm
Time: 1

.0223 Max
0.0198
0.0173
0.0149
0.0124
0.00991
0.00743
0.00496
0.00248
0 Min

C: Control 9 LB1
Total Deformation
Type: Total Deformation
Unit: mm
Time: 1

.0223 Max
0.0198
0.0173
0.0149
0.0124
0.00991
0.00743
0.00496
0.00248
0 Min

A: Control LB1
Equivalent Stress 3
Type: Equivalent (von-Mises) Stress
Unit: MPa
Time: 1

11.536 Max
5
4.375
3.75
3.1251
2.5001
1.8751
1.2501
0.62513
0.00014756 Min

C: Control 9 LB1
Equivalent Stress 4
Type: Equivalent (von-Mises) Stress
Unit: MPa
Time: 1

5.2692 Max
5
4.375
3.75
3.125
2.5
1.875
1.25
0.62501
1.2497e-5 Min

C: Control 9 LB1
Equivalent Stress 3
Type: Equivalent (von-Mises) Stress
Unit: MPa
Time: 1

C: Concept 9 LB1
Equivalent Stress 3
Type: Equivalent (von-Mises) Stress
Unit: MPa
Time: 1

15.122 Max
5
4.375
3.75
3.125
2.5
1.875
1.25
0.62501
1.2497e-5 Min

E: Control 10 LB1
Total Deformation
Type: Total Deformation
Unit: mm
Time: 1

0.113 Max
0.101
0.0882
0.0756
0.063
0.0504
0.0370
0.0252
0.0126
0 Min

E: Control 10 LB1
Total Deformation
Type: Total Deformation
Unit: mm
Time: 1

0.113 Max
0.101
0.0882
0.0756
0.063
0.0504
0.0370
0.0252
0.0126
0 Min

E: Control 10 LB1
Equivalent Stress 3
Type: Equivalent (von-Mises) Stress
Unit: MPa
Time: 1

33.312 Max
1.0
8.75
7.5
6.25
5.0001
3.7501
2.5001
1.2501
0.00013214 Min

E: Control 10 LB1
Equivalent Stress 3
Type: Equivalent (von-Mises) Stress
Unit: MPa
Time: 1

E: Control 10 LB1
Equivalent Stress 3
Type: Equivalent (von-Mises) Stress
Unit: MPa
Time: 1

33.312 Max
1.0
8.75
7.5
6.25
5
3.75
2.5
1.25
0.00013214 Min

DEVICES FOR BONE INTEGRATION

TECHNICAL FIELD

This disclosure relates to fusion surgery and specifically to devices for promoting fusion or supporting bone regions for fusion. The devices have been described in relation to spinal fusion however people skilled in the art will be aware that the device has utility whenever fusion is indicated.

BACKGROUND

Fusion involves positioning a fusion device between two bone regions to support the bone regions and aid in fusion of the regions. Interbody fusion involves positioning an interbody fusion device or cage between two vertebral bodies to restore and maintain spine alignment and disc height and stabilize the spine which aids in fusion of the vertebrae. Commonly a cavity extends through the device. The surgeon deposits bone graft material within the cavity to stimulate or support growth of the bone through the device. The goal is to achieve mechanical stability. Ordinarily this occurs through fusion, as defined by the formation of a solid bone bridge between the two vertebrae, which requires a continuous bone formation and connectivity from one level to the next.

SUMMARY OF THE DISCLOSURE

An improved device for facilitating mechanical stability between two bone regions is described. The device comprises an exterior wall or walls defining an interior cavity. A load arrangement is associated with the device, extending generally inwardly from a device wall into the cavity. This arrangement loads material deposited within the cavity of the device. In use this loading is effective to promote bone remodelling and facilitate fusion and bone integration with the device.

The device influences spinal fusion with respect to graft, device interaction/biomechanics, load transfer between spinal fusion segments, load transfer within the interbody device and finally overall rate of fusion.

In use, the device is positioned between two bone regions. Graft material is positioned within the interior cavity. In some forms, the load arrangement comprises protrusions or plates extending inwardly from the walls to place load on the graft material. In some forms, the protrusions act as a cantilever to place load on the graft or other material in the cavity. In some forms, an elongate element such as a shaft or spring attaches each of the protrusions and places load on them directed into the longitudinal centre of the cavity. In some forms the load arrangement is configured to place load on material in the cavity by loading between a load element and the device wall.

Disclosed is a device adapted to be positioned between two bone regions, the device comprising a cage having at least one wall defining at least one interior cavity, and, a load arrangement comprising at least one interacting element configured to interact with either a second interacting feature or the wall to load material positioned within the cavity.

In some forms, load is placed on material within the cavity by biasing the parts of the load arrangement toward one another or toward the wall. This bias may result from shaping the protrusions to effect an inwardly directed force, by selecting material to effect an inwardly directed force and/or by attaching an engagement body that effects a force on the load arrangement, among other methods of biasing.

In some forms, a loading member may be situated to redirect load from an endplate of the device to press against or abut the loading element in the cavity. In some forms this deforms or otherwise angles the loading element to load the graft. In some forms the load may be transmitted linearly or non-linearly, in some forms the load may be transmitted dynamically and loading may change during use. In some forms the loading elements transmit and/or resist torsional loading.

In some forms the loading member comprises a protrusion extending into the cavity from at least one wall. In some forms the load arrangement comprises a plurality of load elements extending into the cavity from at least one wall of the cage. In some forms each load element is substantially planar and biased toward the longitudinal centre of the cavity.

In some forms the load arrangement comprises at least one load element extending into the cavity from the wall and at least one elongate member extending from the load element and effecting a force to pull the element inwardly toward a central point within the cavity.

In some forms the load arrangement comprises two load elements positioned proximal opposing ends of the cage and the elongate member extends between the load elements to facilitate load between the load elements, effecting a force to pull the element inwardly toward a central point within the cavity.

In some forms the elongate member comprises a spring. The spring has the advantage of controlling stiffness.

In some forms at least a portion of the load arrangement is degradeable.

Further, disclosed is a method of promoting stability in bone comprising positioning a device as defined in claim 1 between two bone regions; placing graft material within the cavity of the device such that the load arrangement places load on the graft material within the cavity. The device is configured for load to be placed on material positioned within the cavity.

The load on the graft or other material has the potential advantages of improving and speeding remodelling of bone, directly loading the graft materials, mechanically stabilising the device and the spine, producing a stable and rigid spine more rapidly than with a conventional interbody device and allowing graft to be loaded such that the bone remodels and is maintained throughout the healing process.

BRIEF DESCRIPTION OF THE FIGURES

Embodiments will now be described by way of example only, with reference to the accompanying drawings in which.

DETAILED DESCRIPTION OF EMBODIMENTS

Figure 1:
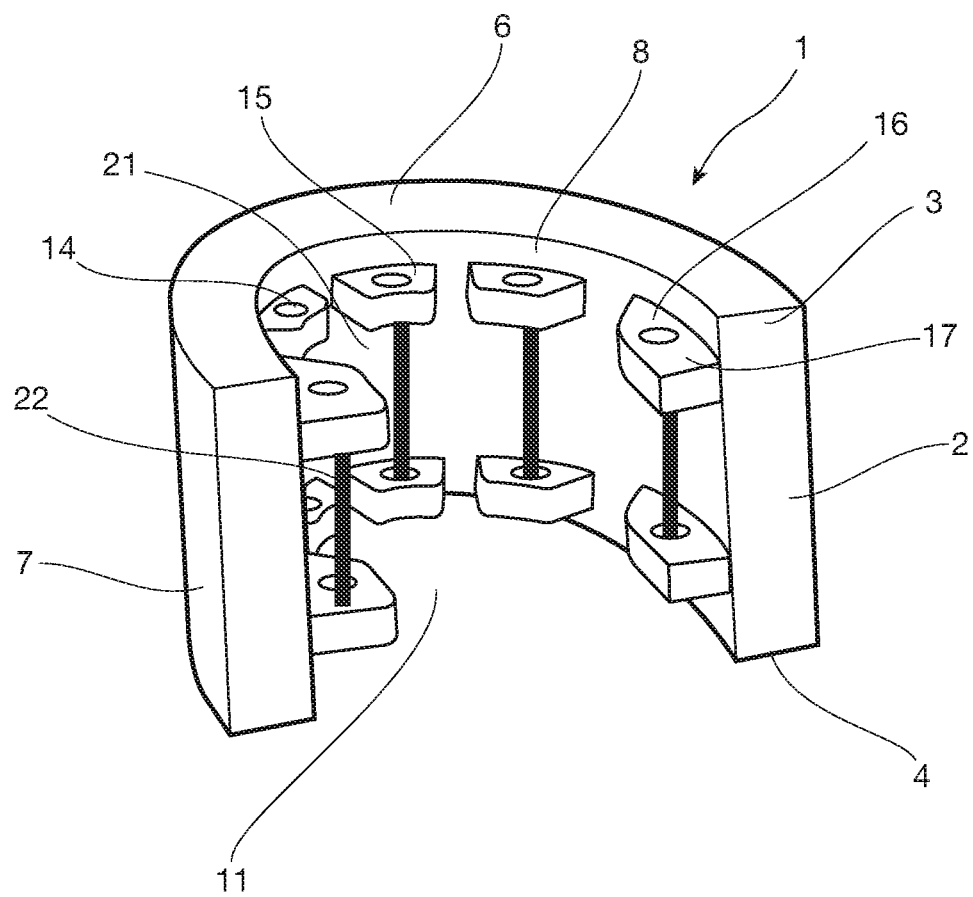
FIG. 1 is a top perspective cut away view of a device of one embodiment of the disclosure.

In some forms, disclosed is a device adapted to be positioned between two bone regions, the device comprising a cage having at least one wall defining at least one interior cavity, and, a load arrangement comprising at least one loading element configured to interact with either a second loading element or the wall to load material positioned within the cavity.

In some forms the load element is any interacting feature.

In some forms the load element extends into the cavity from at least one wall.

In some forms the load element is positioned with respect to the wall such that it acts as a cantilever.

In some forms the load arrangement comprises a plurality of load elements extending into the cavity from at least one wall of the cage.

In some forms each load element has two planar faces extending substantially parallel to one another from the wall.

In some forms each load element comprises a plate.

In some forms the load elements are deformable.

In some forms the load arrangement comprises a plurality of load elements in the form of interacting features, the interacting features being tapered.

In some forms the load arrangement comprises at least one load element extending into the cavity from the wall and at least one elongate member extending from the load element.

In some forms the load arrangement comprises two load elements extending into the cavity from the wall and the elongate member extends between the load elements to facilitate load between the load elements.

In some forms the load elements are positioned proximal opposing ends of the cage In some forms the elongate member extends longitudinally with respect to an axis extending through the cavity from one load element to the other.

In some forms the elongate member extends beyond the load elements in at least one direction.

In some forms the elongate member comprises a spring.

In some forms the elongate member comprises a post of circular or geometric cross section.

In some forms the elongate member comprises a bowed or curved shaft.

In some forms the load arrangement is biased toward a centre of the cavity.

In some forms the elongate member biases the load elements toward one another.

In some forms the load arrangement is degradeable.

In some forms the device further comprises an insertable divider to divide the cavity into a plurality of sections.

In some forms at least a portion of the load arrangement is composed of titanium or other metals.

In some forms at least a portion of the load arrangement is composed of a degradable polymer.

In some forms the degradable polymer includes an active agent which is released as the polymer degrades.

In some forms, disclosed is a method of promoting stability in bone comprising:

positioning a device as defined in claim 1 between two bone regions; placing graft material within the cavity of the device such that the load arrangement places load on the graft material within the cavity.

Generally the application discloses a device including features that, when the device is filled with bone graft or other material, comprise a load arrangement that loads the graft material within the cavity. The load arrangement is also configured such that ingrowth, outgrowth or ongrowth of bone effects mechanical engagement of the bone to the device. In some cases, this mechanical engagement means that bone to bone union is not essential to provide the practical effects of fusion.

This has the advantage of increasing speed and effectiveness of remodeling bone within the cavity, thus improving stability between the bone region or vertebral body and the device which may result in bone or spinal stability at an earlier stage, improvement in load distribution and greater stability between the device and the bone region or vertebral body.

In some forms, loading on the graft material may have benefits such as facilitating bony remodeling and new bone formation, providing a symmetrical load, moving the stresses on the device toward the interior of the vertebral body, limiting hotspots, reducing subsidence of the graft material, improving overall biological activity and increasing the speed of fusion.

The load arrangement may be in the form of load elements such as protrusions of various geometric arrangements, plates or shoulders extending from the wall of the device into the interior cavity of the device. In some forms the load elements are positioned in the interior of an internal cavity extending through the device. In some forms the load elements extend part or full way across the cavity. In some forms the load elements are removably attached with the device or removably extend through the device. In some forms the features may be inserted or engaged with the body of the device before or during surgery.

In some forms the load arrangement comprises a plurality of protrusions extending inwardly from an interior surface of the cavity. In some forms the protrusions are positioned proximal an end of the device. In some forms the protrusions include holes extending therethrough or openings or notches extending therethrough.

In some forms the load arrangement further includes an elongate member extending between load elements positioned proximal either end of the device or between the load element and the interior wall of the device. In some forms the elongate member is in the form of a spring, a rod, a bowed shaft or alternate shaped elongate member. In some forms the elongate member is engaged with two load elements or with a load element and the wall of the device to change the mechanical environment experienced by the graft within the cavity.

In some forms the load arrangement is at least in part degradable, and composed of a degradable polymer. In some forms the load arrangement releases a material such as a growth factor or antibiotic upon degrading. In some forms the load arrangement or a portion thereof is composed of titanium or other metal.

In use, graft may be inserted into the cavity in vivo. In some forms the graft material is autograft, allograft, synthetics or any kind of graft material.

Referring now to FIG. 1, in one embodiment the disclosure provides an interbody device 1. designed to be positioned between two vertebral bodies, the device comprising a body 2 extending between a first end 3 and a second end 4. The body 2 is generally sized and shaped to be positioned between vertebral bodies. In this embodiment the body comprises a curved wall 6 defined by an outer surface 7 and inner surface 8 extending between the first end 3 and the second end 4.

In some forms the body 2 is composed of polyether ether ketone, polylactides or biocompatible polymers, carbon-fibre composites, titanium, polyethylene, silicon nitride, or allograft, xenograft, autograft or other biologically compatible materials.

In this illustrated embodiment the body includes an internal cavity 11 extending between the two ends. The internal cavity 11 is defined by the inner surface 8 of the body. The inner surface 8 includes a load arrangement 14 in the form of a plurality of load elements 15 extending into the cavity and positioned generally proximal either end of the interior cavity 11.

In this embodiment the load elements 15 include a cavity 16 extending therethrough. The load elements extend generally laterally with respect to the interior cavity 11 and extend into the interior cavity from the interior wall 8. The load elements generally comprise two surfaces 17 and 17' in facing arrangement and running generally parallel to one another.

It will be clear, however, that load elements of various shapes and geometries fall within the scope of the disclosure, For example, a plate, a bar, a mesh or ridge or tapered point are all viable.

The load elements 15 create a load region 21 located between the load elements in the interior cavity.

In the illustrated form, the load arrangement 14 further includes a plurality of elongate members 22 located intermediate and extending between the load elements 15. The elongate members change the mechanical environment in the load region 21 and bias the load elements 15 toward one another and the longitudinal centre of the cavity. This increases the load in the load region.

It will be clear that the load elements 14 and elongate members 22 act together to effect the load in the load region 21. Changes in the composition of the load elements and the elongate members impacts the stiffness of this region and the load. The position of the elongate members 22 with respect to the load elements 15 also has an impact on the stiffness of the central portion of the device.

The stiffness of the device and regions of the device may also be impacted by the thickness of the elongate member material and the thickness of the load element material.

In some forms the elongate members are composed of degradable material which allows the release of materials and also allows the stiffness of the device to change over time.

In the illustrated form the elongate members are simple rods, however the elongate members can be in the form of springs, rod spring combinations, tubes, or other geometric forms.

In use, an interbody device is selected for qualities of stiffness and load as required by the surgeon. The interbody device is positioned between two vertebral bodies. Bone graft material is deposited within the internal cavity 11 to stimulate bone growth from the vertebral bodies. In this embodiment, bone growing into the internal cavity 11 of the body 2 may grow around the load elements 15 causing bone ingrowth around the laterally extending surface 17. Bone remodelling within the interior cavity 11 is impacted by the load region 21 and the load placed on the bone graft through the load arrangement 14.

The device promotes containment of material such as bone graft within the device. Moreover it allows for an increase in loading on the graft material which impacts the process of bone remodelling.

The elongate members extending from the load elements foster an active, dynamic system by changing the mechanical environment of the material in response to forces on the device. The material of the elongate member and the load elements is deformable allowing for a dynamic device. When the device is loaded it resists deformation. The deformation also assists in delivering nutrients to the local tissues through movement of fluids due to deformation.

Figure 2:
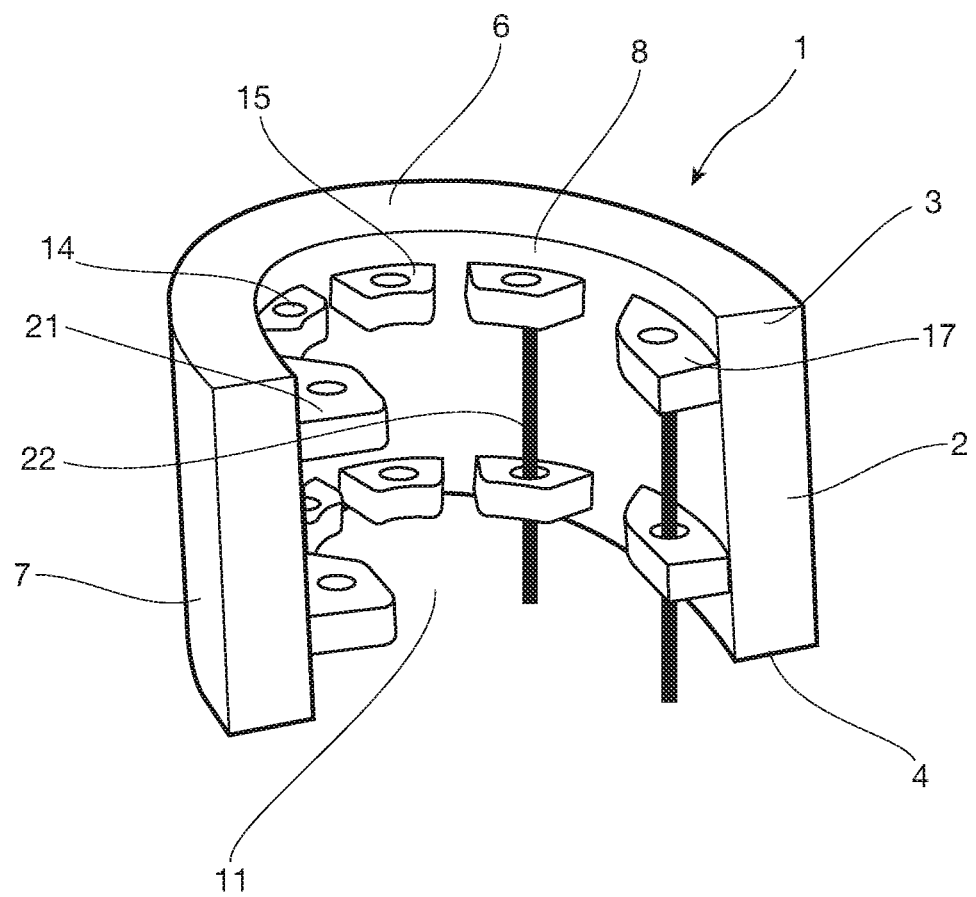
FIG. 2 is a top perspective cut away view of a device of a second embodiment of the disclosure.

Referring now to FIG. 2, disclosed is an interbody device 1 comprising a body 2 extending between a first end 3 and a second end 4. As in the first embodiment, in this embodiment the body comprises a curved wall 6 extending between the first end 3 and the second end 4.

In this illustrated embodiment the body includes an internal cavity 11 extending between the two ends. The internal cavity 11 is defined by an internal surface 8 of the body. The internal surface 8 includes a load arrangement 14 in the form of load elements 15 extending into the cavity 11.

In the illustrated form, the load arrangement 14 further includes a plurality of elongate members 22 located intermediate and extending between and beyond the load elements 15. The elongate members change the mechanical environment in the load region 21 and bias the load elements 15 toward one another and the longitudinal centre of the cavity. This increases the load in the load region.

Figure 3:
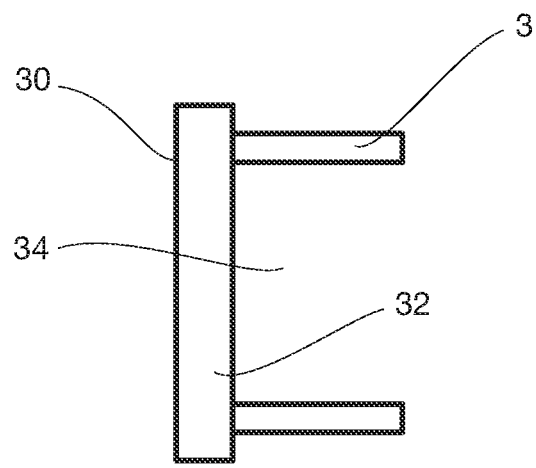
FIG. 3 is a cross sectional section view of a third embodiment of the disclosure.

Referring now to FIG. 3, disclosed is an interbody device 30, shown here in section of a cross-section. The device 30 includes a plurality of load elements 31 extending outwardly from an internal wall 32 of the device, The load elements extend a substantial portion of the distance between the internal wall 32 and the opposite internal wall (not illustrated). The load elements 31 create a load region 34 intermediate the load elements.

Figure 4:
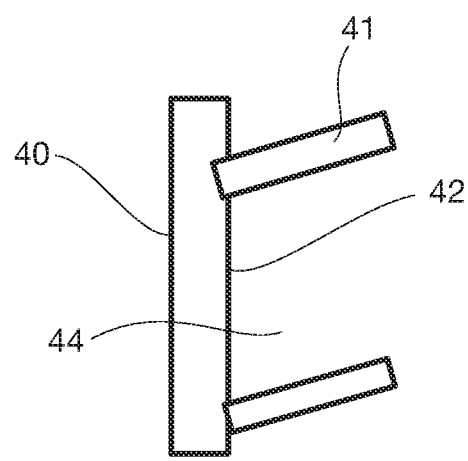
FIG. 4 is a cross sectional section view of a fourth embodiment of the disclosure.

Referring now to FIG. 4, disclosed is an interbody device 40 shown here in section of a cross-section. The device 40 includes a plurality of load elements 41 extending outwardly from an internal wall 42 of the device. The load elements are angled and extend a substantial portion of the distance between the internal wall 42 and the opposite internal wall (not illustrated). The load elements 41 create a load region 44 intermediate the load elements.

Figure 5:
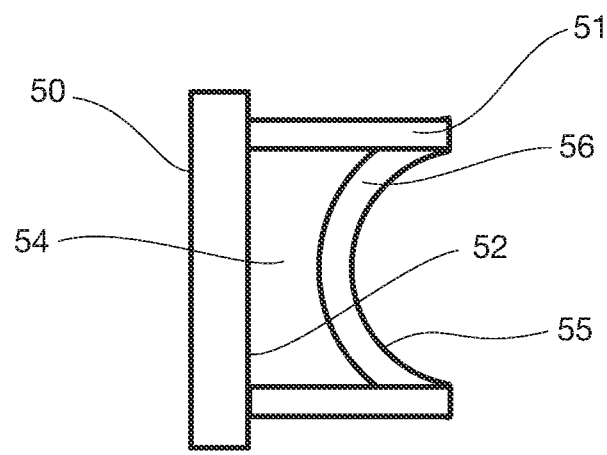
FIG. 5 is a cross sectional section view of a fifth embodiment of the disclosure.

Referring now to FIG. 5, disclosed is an interbody device 50 shown here in section of a cross-section. The device 50 includes a plurality of load elements 51 extending outwardly from an internal wall 52 of the device. The load elements extend a substantial portion of the distance between the internal wall 52 and the opposite internal wall (not illustrated). The load elements 51 create a load region 54 intermediate the load elements. An elongate element 55 in the form of a bowed shaft 56 is located between the load elements 51.

In use, the interbody device 50 is positioned between two vertebral bodies. Bone graft material is deposited within the internal cavity in the load region 54 to stimulate bone growth from the vertebral bodies. In this embodiment bone graft positioned in the load region is put under load by the load elements 51 and the elongate member 55 which acts to connect the load elements 51 and increase load. In some embodiments and cases bone to bone union will not be required to produce stability between the bones.

Figure 6:
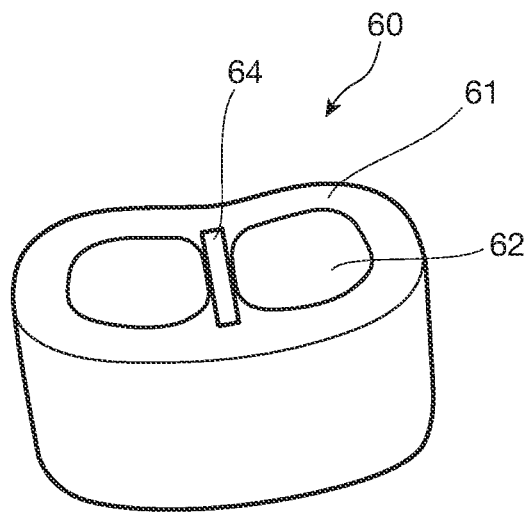
FIG. 6 is a top perspective view of a sixth embodiment of the disclosure.
Figure 7:
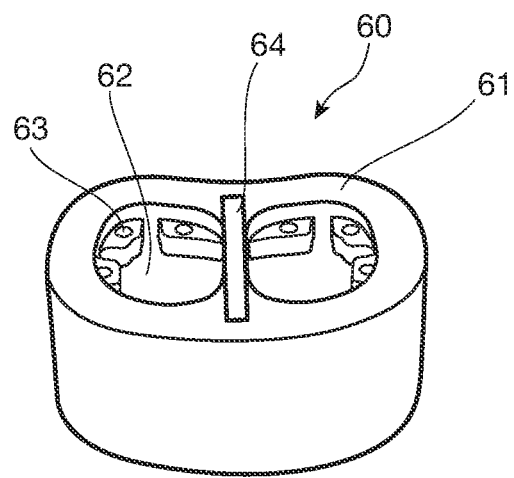
FIG. 7 is a top perspective view of a seventh embodiment of the disclosure.
Figure 8:
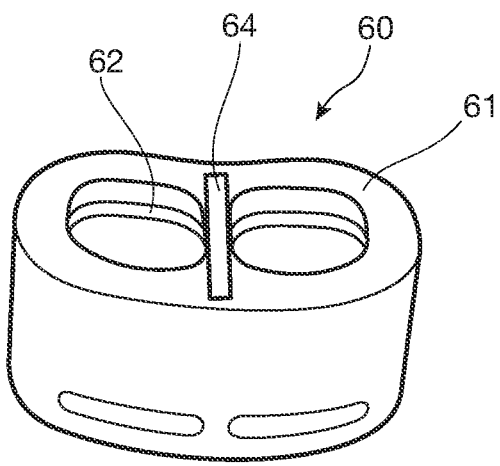
FIG. 8 is a top perspective view of an eighth embodiment of the disclosure.

Referring now to FIGS. 6-8, disclosed is an interbody device 60 comprising at least one wall 61 defining an interior cavity 62. The interior cavity may contain protrusions in the form of load or stabilising elements 63. The cavity 62 may have an insert 64 that in some forms is removably inserted therein to divide the cavity into sections.

Figure 9:
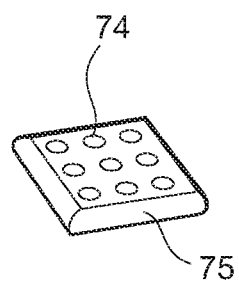
FIG. 9 is a top perspective view of an insert of one embodiment of the disclosure.

As shown in FIG. 9, the divider 74 may be in the form of a titanium or other metal or polymer plate 75. Alternatively the divider may be any other bio-suitable material.

In some forms and cases the present device may allow for symmetrical loading or may shift the loading into the graft or cage or vertebral body.

Examples

Figure 10:
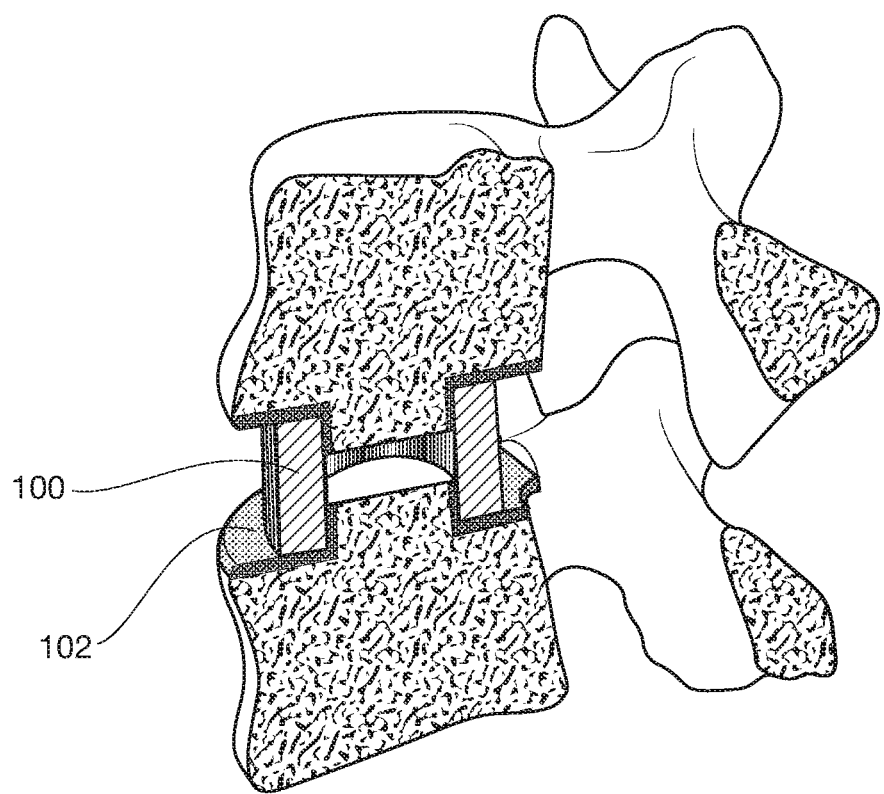
FIG. 10 is a cross sectional view of a control device in vivo.

FIG. 10 shows a control PEEK interbody device 100 with a non-union between the levels. This is modeled in the current case by the lack of bony continuity between the two vertebral bodies. A gap is present in the middle of the interbody device that represents the case of a delayed or non-union. There is also a gap 102 present at the interface of the bone and the PEEK interbody cage that represents the fibrous tissue, that is present between bone within the cage and the PEEK device.

Integration between the two levels is not present. The spine is not fused.

Figure 11:
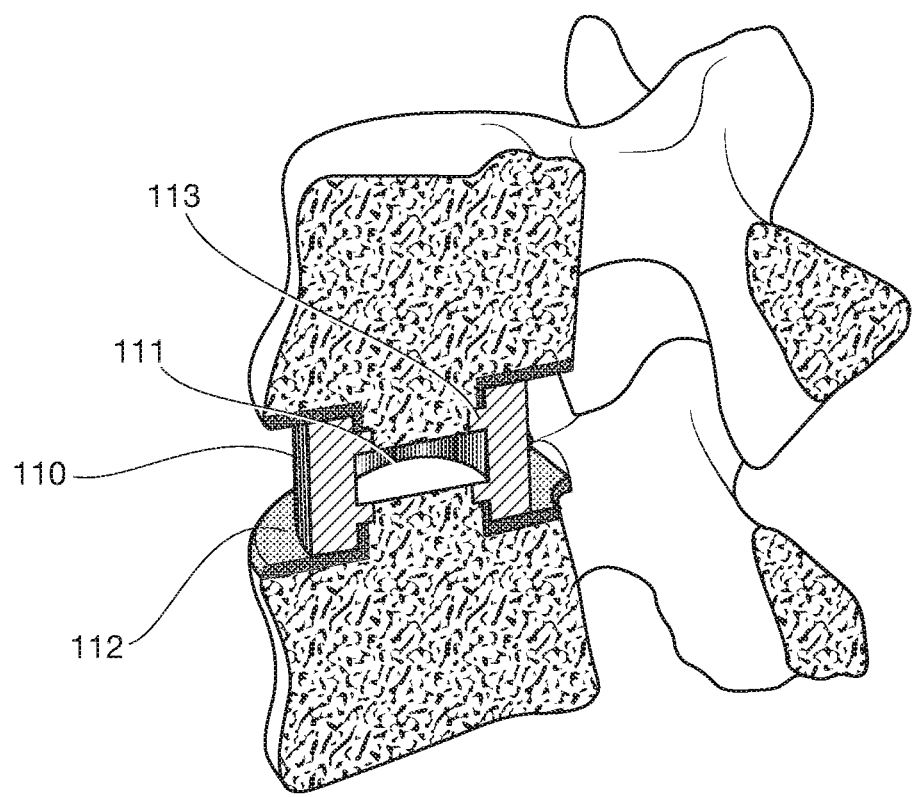
FIG. 11 is a cross sectional view of a device of one embodiment of the disclosure in vivo.

FIG. 11 shows a KNOB device 110 in the same case of delayed or non-union as FIG. 10. A delayed or non-union is modeled by the lack of bony continuity between the two vertebral bodies. A gap 111 is present in the middle of the interbody device that represents the case of a delayed or non-union. There is also a gap 112 present at the interface of the bone and the PEEK interbody cage that represents the fibrous tissue, that is present between bone within the cage and the PEEK device.

In this case of the KNOB design however, unlike the control PEEK cage, there is direct integration of the bone from the vertebral body directly with the interbody cage on the upper and lower levels that enables fusion to be achieved. This relies upon healing of the graft material that is placed within the cage itself that "heals" the local host bone on the upper and lower segments.

The interior knobs within the cage provide the unique features that differentiated from the standard PEEK cage shown in FIG. 10.

The internal features of the device 110 provide a number of benefits with respect to graft loading, and plate loading, on, in and through fixation and overall the distribution to facilitate a more rapid and more robust and long-lasting fusion.

Figure 12:
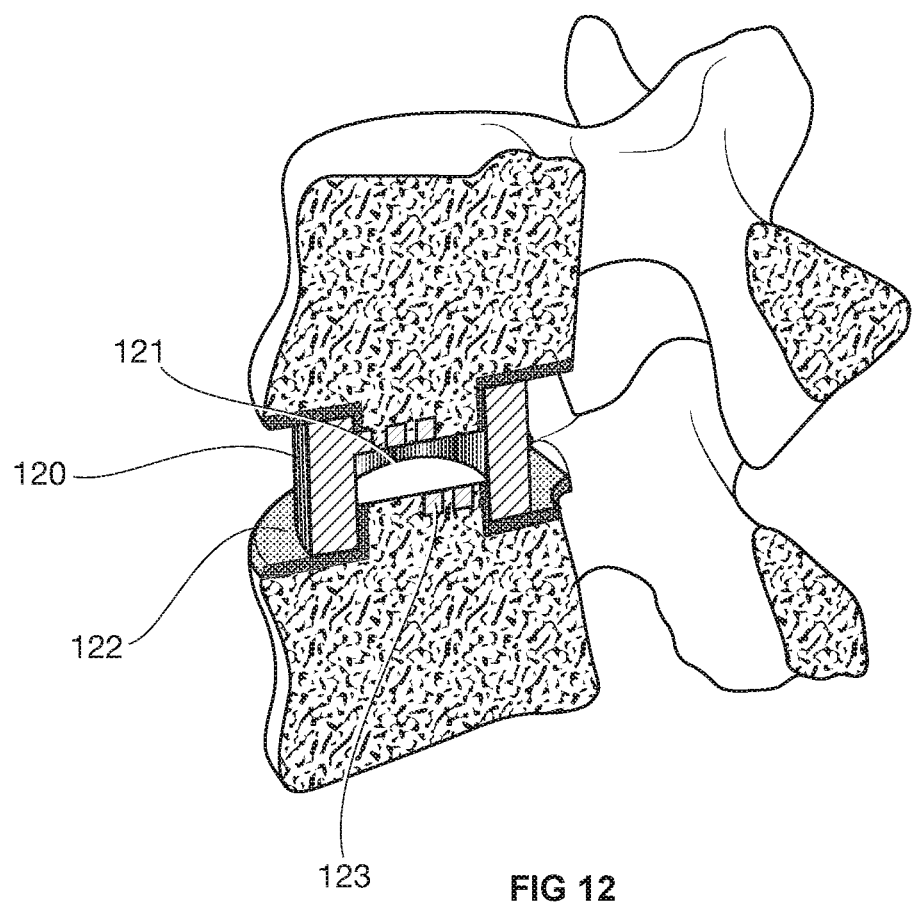
FIG. 12 is a cross sectional view of a device of another embodiment of the disclosure in vivo.

FIG. 12 shows a delayed or non-union modeled by the lack of bony continuity between the two vertebral bodies. A gap 121 is present in the middle of the interbody device 120 that represents the case of a delayed or non-union. There is also a gap 122 present at the interface of the bone and the PEEK interbody cage that represents the fibrous tissue, so called PEEK-Halo, that is present between bone within the cage and the PEEK device.

In this case of the device has a Ti plate 123 incorporated into the design. There is therefore direct integration of the bone from the vertebral body directly with the interbody cage 120 on the upper and lower levels that enables fusion to be achieved. This relies upon healing of the graft material that is placed within the cage itself that "heals" the local host bone on the upper and lower segments.

Figure 13:
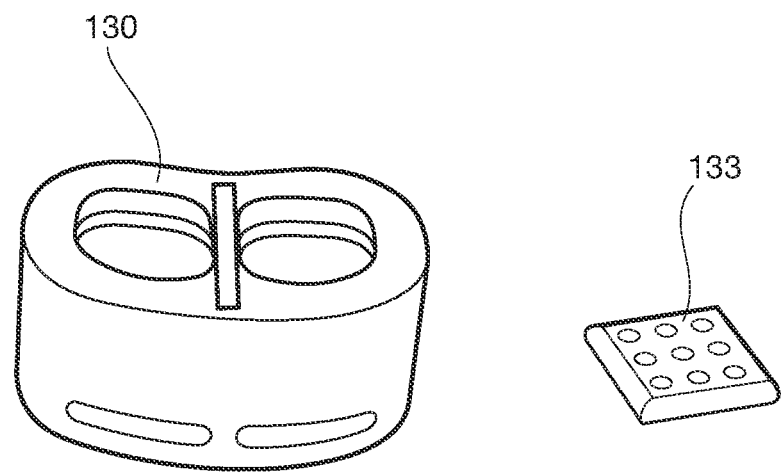
FIG. 13 is a perspective view of a device of a further embodiment of the disclosure.
Figure 14:
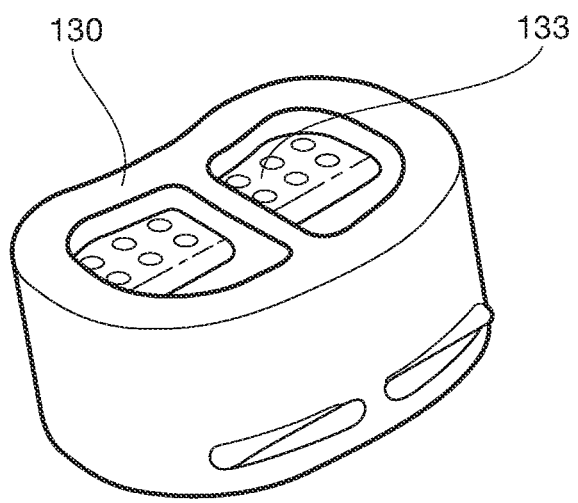
FIG. 14 is a perspective view of a device of a further embodiment of the disclosure.

FIGS. 13 and 14 show one embodiment of the interbody device 130. The interior Ti Plates 133 within the cage provide the unique features that differentiated from the standard PEEK cage shown in FIG. 10. The internal features of the device provide a number of benefits with respect to graft loading, and plate loading, on, in and through fixation and overall the distribution to facilitate a more rapid and more robust and long-lasting fusion.

In some not illustrated forms, a loading member or an elongate member extends between endplates or between a portion of the wall and an endplate to place load on the material in the cavity.

In some not illustrated forms, the cavity is shaped to encourage load place on the material. In some forms, movement of a loading element into the cavity effects load on the material in the cavity.

In some forms, the device comprises a wall defining an interior cavity, a plurality of load elements extending from the wall and defining or partially defining a load region within the interior cavity, the load region a section of the interior cavity that is configured such that the load on material deposited in the load region is greater than the load on material external to the load region. In some forms, the load elements are biased into the load region to place load on material in the load region. In some forms, the load elements are positioned to place load on material in the load region.

FIGS. 15-19 show finite element modelling results presented for the control case of a PEEK interbody device with a fibrous tissue interface and lack of complete union as more often than not observed in the clinical scenario. The results presented for global deflection, as well as von Mises stress distribution. The results demonstrate the asymmetric nature of loading in the absence of fusion as well as the presence of hotspots when looking more closely at the interface between the cage and the endplate itself. The spine is not fused. The results reflect the lack of fusion and stabilization. Areas of hotspots are present on the vertebral bodies due to the asymmetry of loading. This theoretically would drive the bone to a different status quo that could ultimately lead to increased subsidence and/or lack of biological activity due to the differences in learning and in this case the lack of it due to the unloading.

Figure 15:
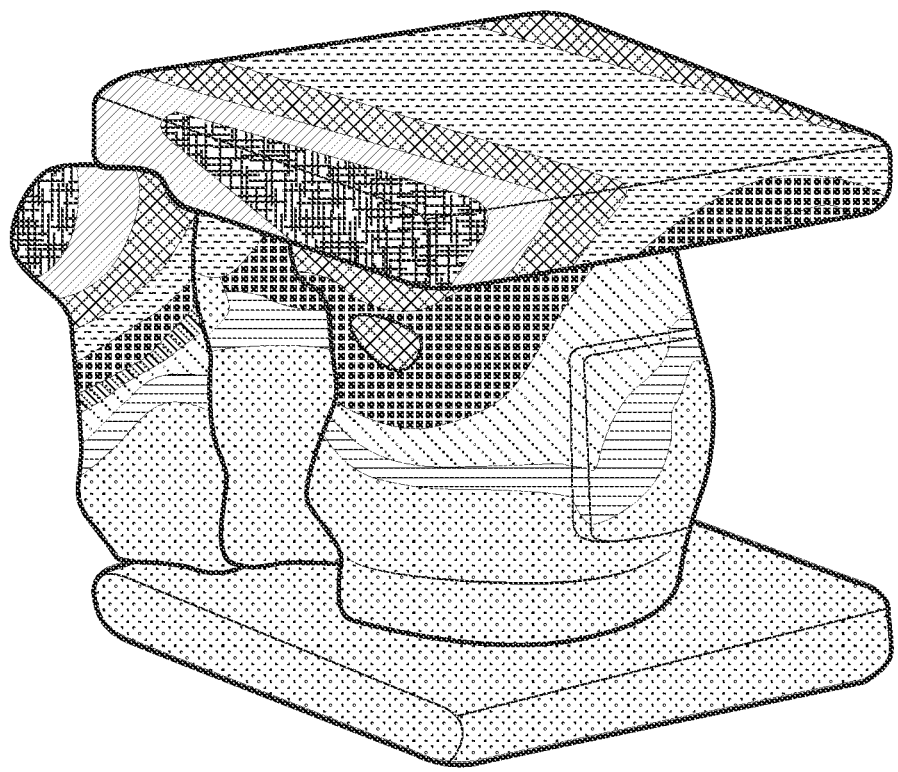
FIG. 15 shows a global deflection iso view for a control.
Figure 15:
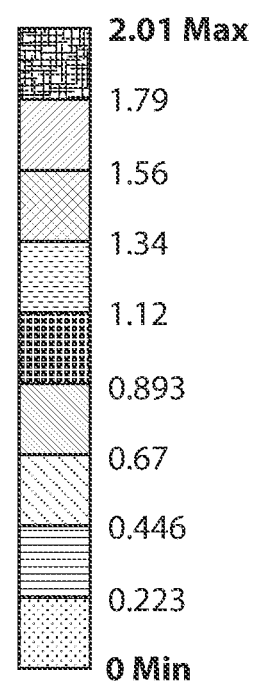
Figure 16:
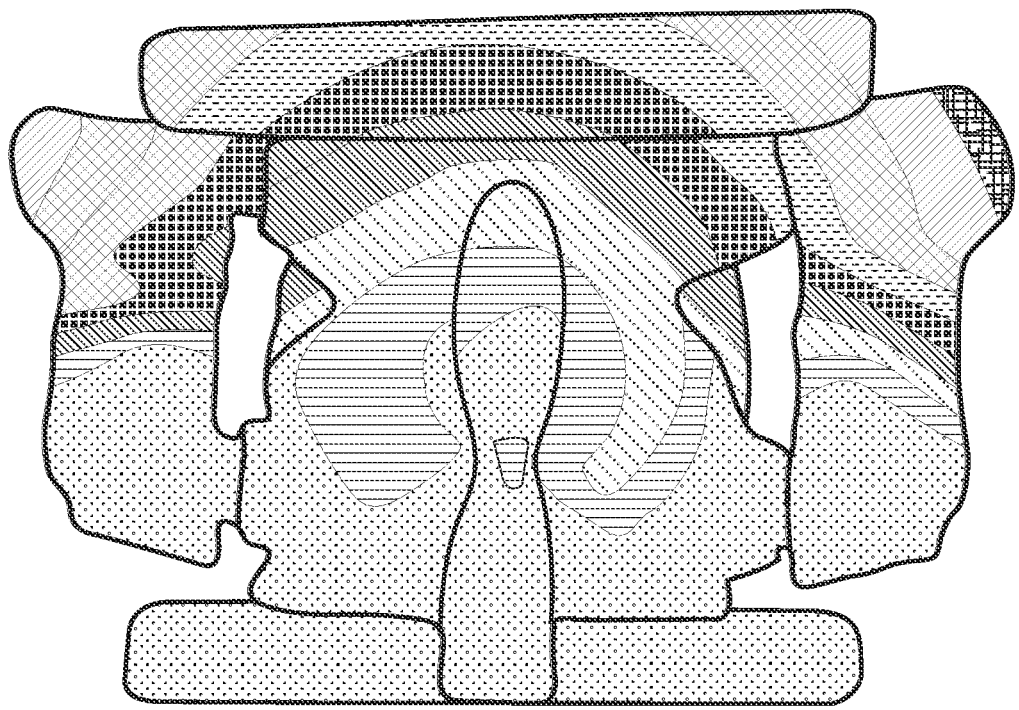
FIG. 16 shows a global deflection posterior view for a control.
Figure 16:
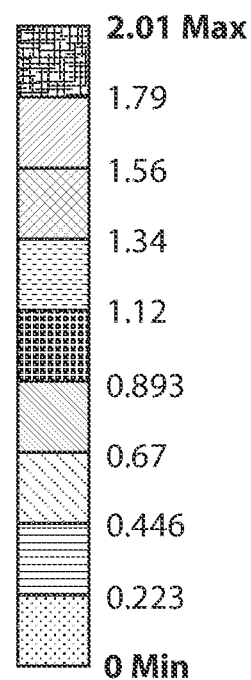
Figure 17:
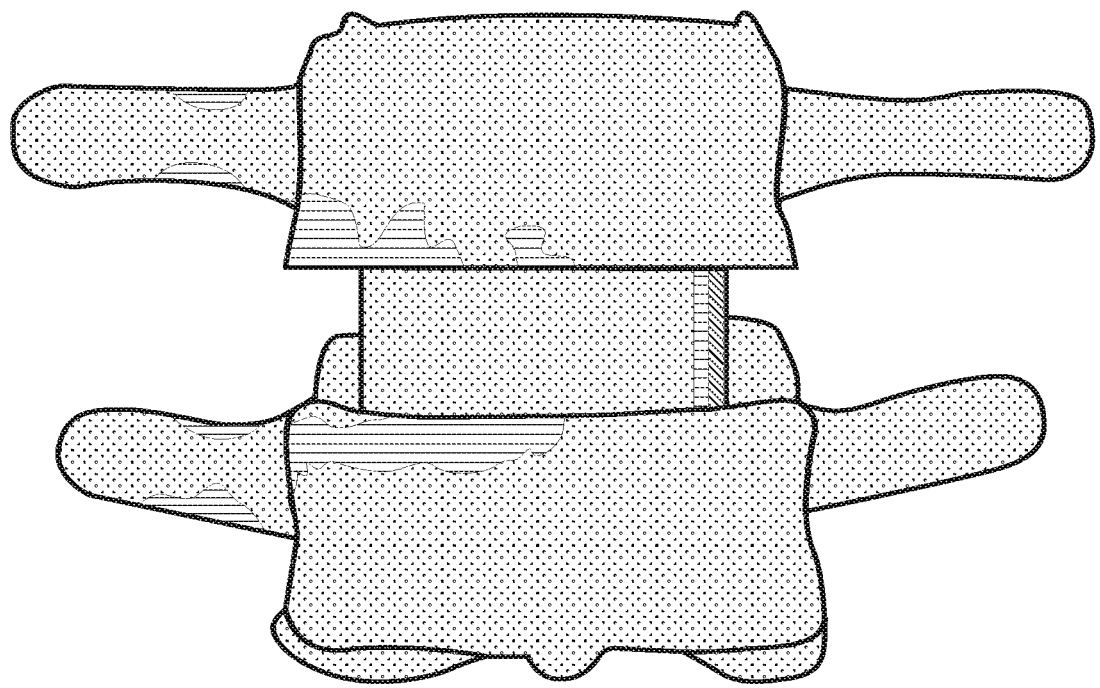
FIG. 17 shows Von Mises stress for lateral bending for a control.
Figure 17:
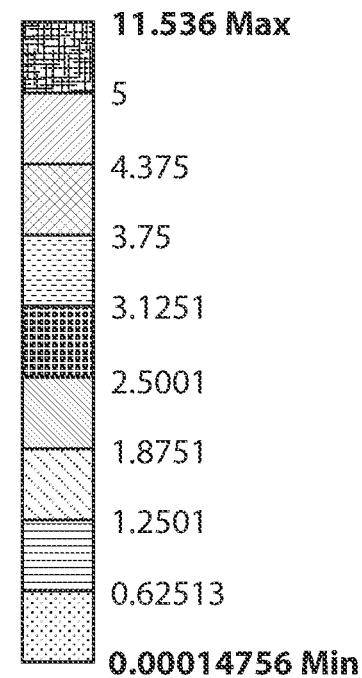
Figure 18:
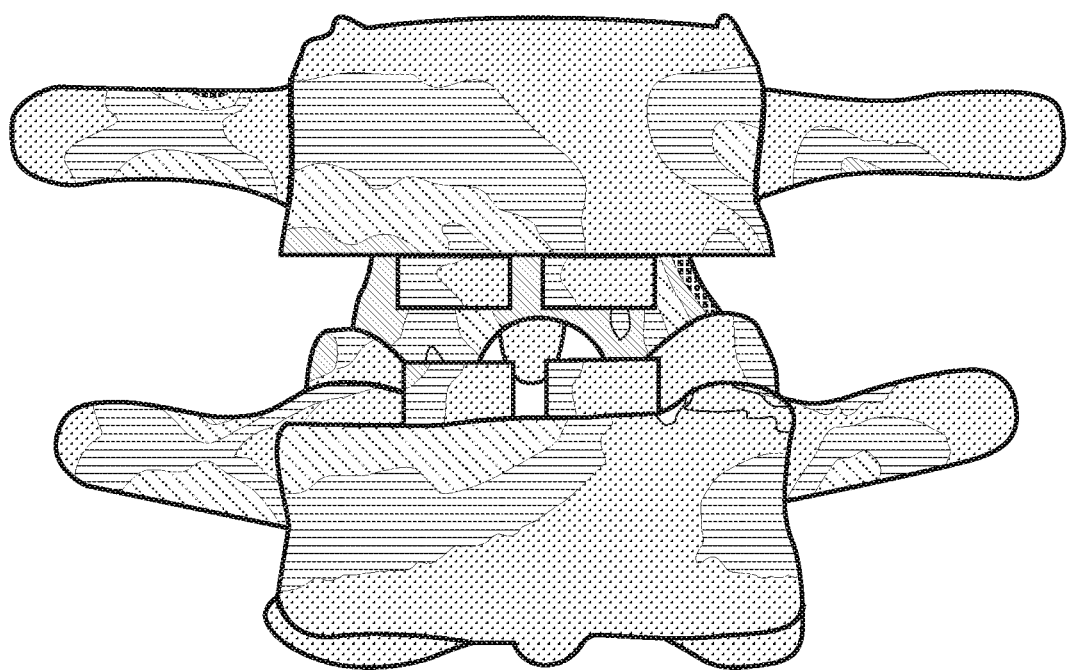
FIG. 18 shows Von Mises stress for a control with the cage removed.
Figure 18:
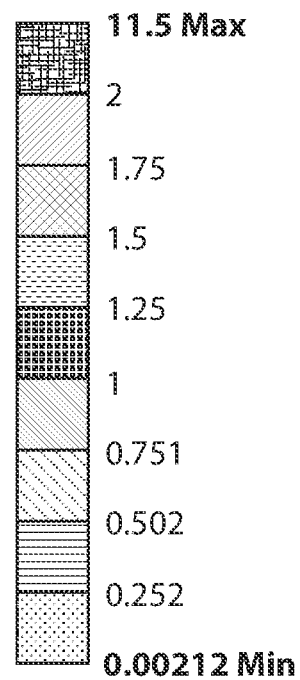
Figure 19:
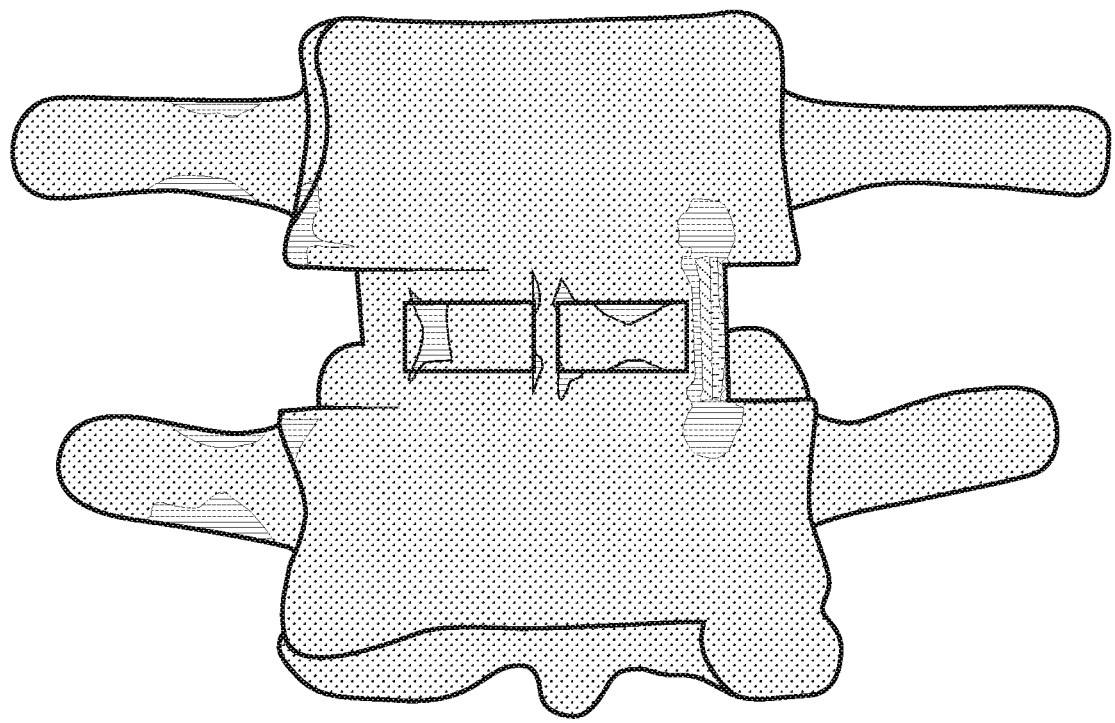
FIG. 19 shows Von Mises stress for lateral bending for a control.
Figure 19:
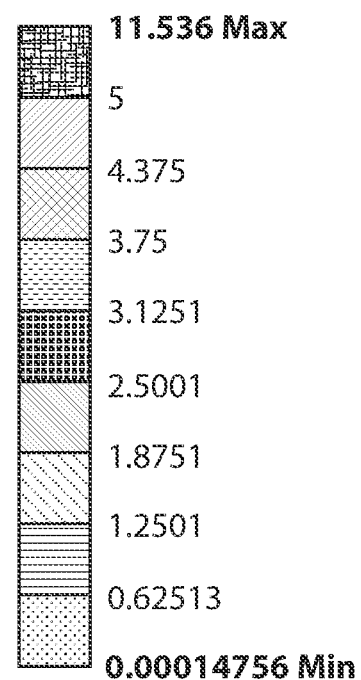

FIG. 15 shows a global deflection iso view and FIG. 16 shows a global deflection posterior view. FIG. 17 shows Von Mises stress for lateral bending demonstrating asymmetric stress distribution. FIG. 18 shows Von Mises stress with the cage removed demonstrating the stress distribution on the graft itself for lateral bending. Clearly, the graft inside the cage is barely loaded and there is an overall asymmetric load distribution. This reflects the lack of fusion and stabilization. This lack of loading of the graft within the cage also would result in a lower overall biological remodeling input due to mechanical influence and potentially increased graft resorption due to the lack of loading itself. FIG. 19 shows Von Mises stress for lateral bending demonstrating asymmetric stress distribution. This reflects the lack of fusion and stabilization. This so-called hotspot the finite element modelling (arrow) can potentially lead to subsidence due to increased stress at the interface with the endplate.

FIGS. 20-30 show the results for a device with internal features, specifically the concept including a titanium plate. The results presented show global deflection, as well as von Mises stress distribution. The interior knobs within the cage provide the unique features that differentiated from the standard PEEK cage shown in FIG. 1. The internal features of the device provide a number of benefits with respect to graft loading, and plate loading, on, in and through fixation and overall the distribution to facilitate a more rapid and more robust and long-lasting fusion.

The internal features not only facilitate fusion of the spine but also provide a new and novel distribution of the forces both within the graft material as well as the implant itself.

Figure 20:
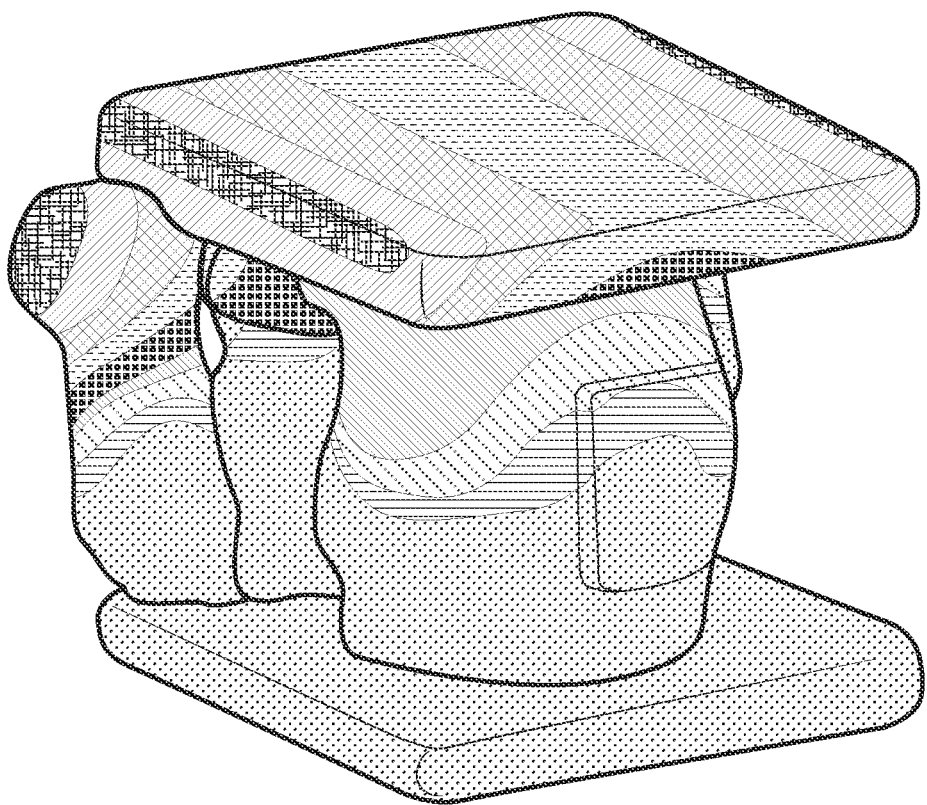
FIG. 20 shows global deflection iso view for one embodiment of the disclosure.
Figure 20:
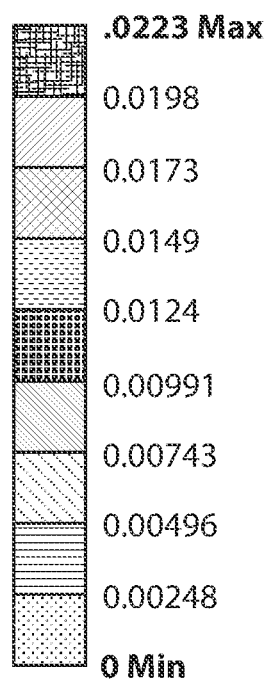

FIG. 20 shows global deflection iso view which is virtually 0 and markedly different compared to the control, non-fused case as shown standard peek cage condition.

Figure 21:
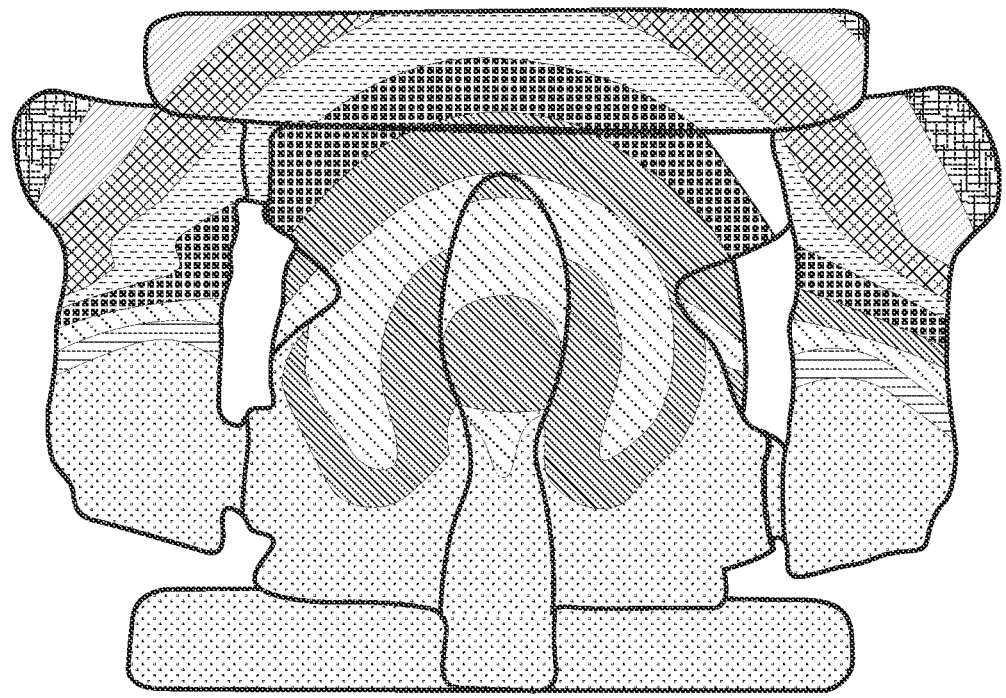
FIG. 21 shows deflection posterior view for one embodiment of the disclosure.
Figure 21:
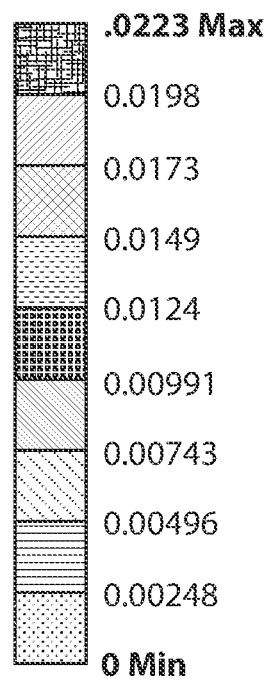

FIG. 21 shows deflection posterior view and is virtually 0 and markedly different compared to the control, non-fused case as shown standard peek cage condition.

Figure 22:
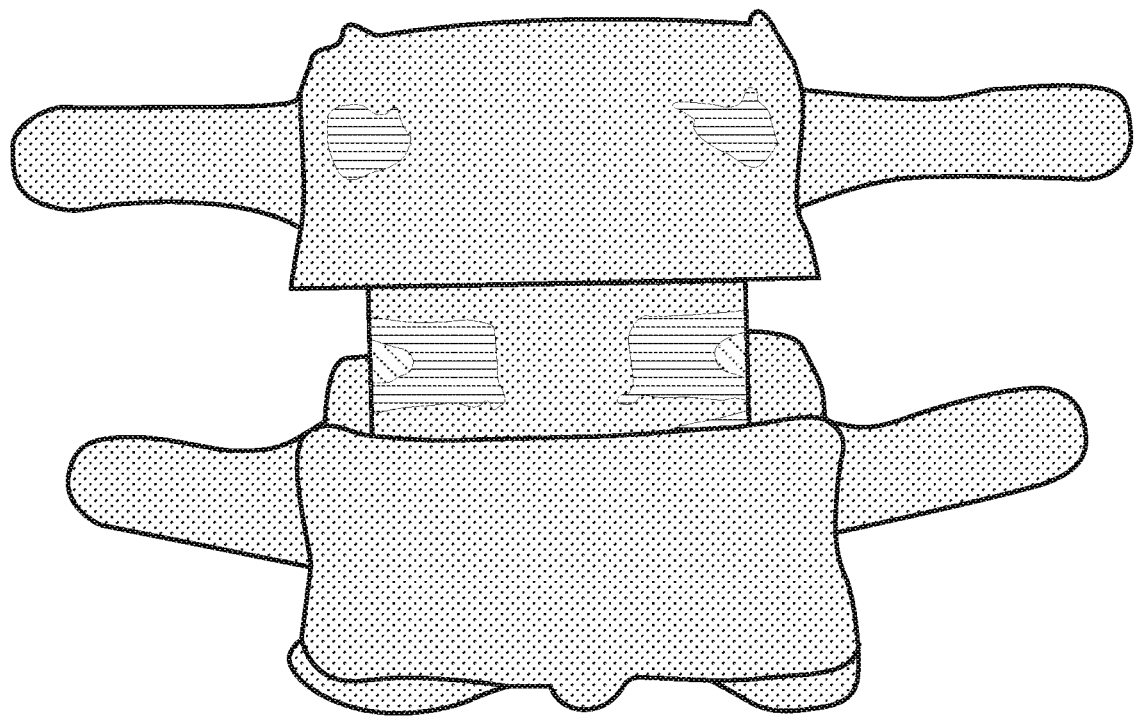
FIG. 22 shows Von Mises stress for one embodiment of the disclosure.
Figure 22:
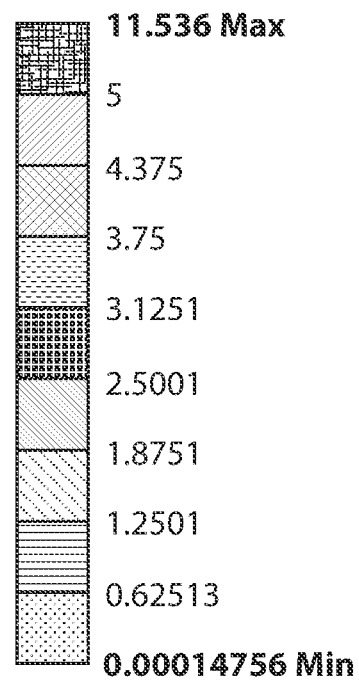

FIG. 22 shows Von Mises stress and demonstrates the symmetry of the load both on the vertebral body as well as within the cage itself.

Figure 23:
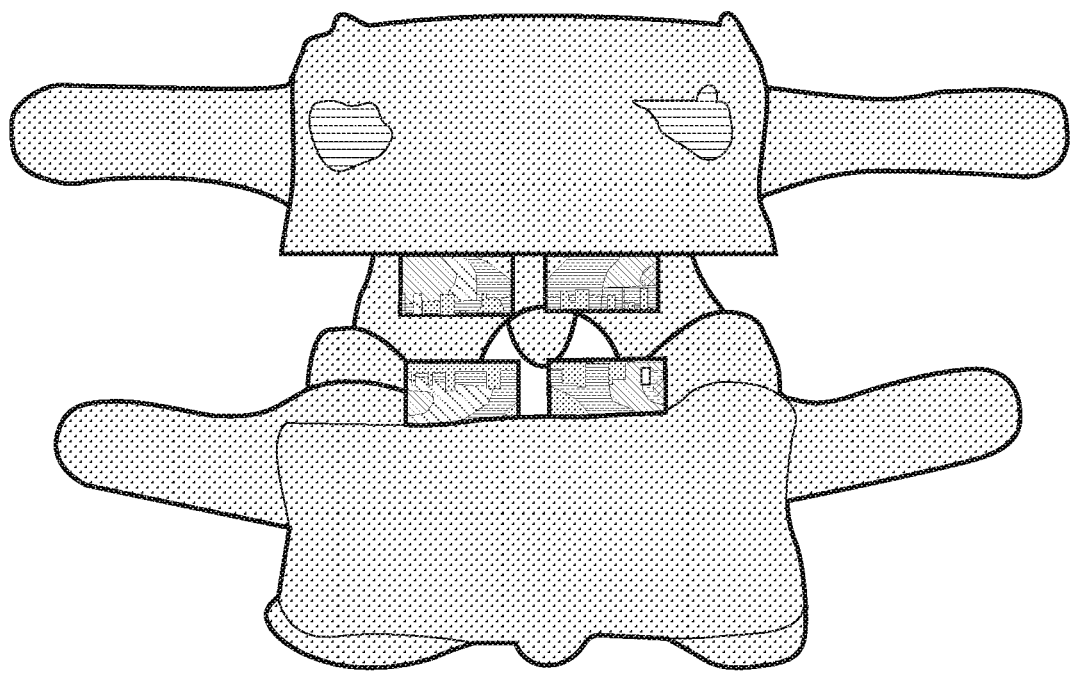
FIG. 23 shows Von Mises stress with the cage removed for one embodiment of the disclosure.
Figure 23:
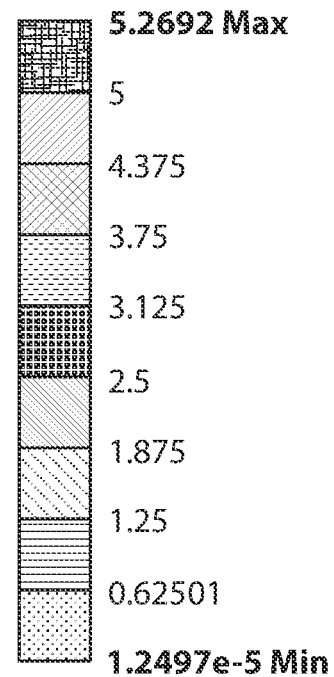

FIG. 23 shows Von Mises stress with the cage removed and only examining the interior graft that has fill the cage again. This demonstrates the symmetry of loading both within the graft itself as well as on the vertebral body. The graft within the cage is being loaded which would facilitate bony remodeling and new bone formation. This is in stark contrast to that of the PEEK control cage shown in the case above.

Figure 24:
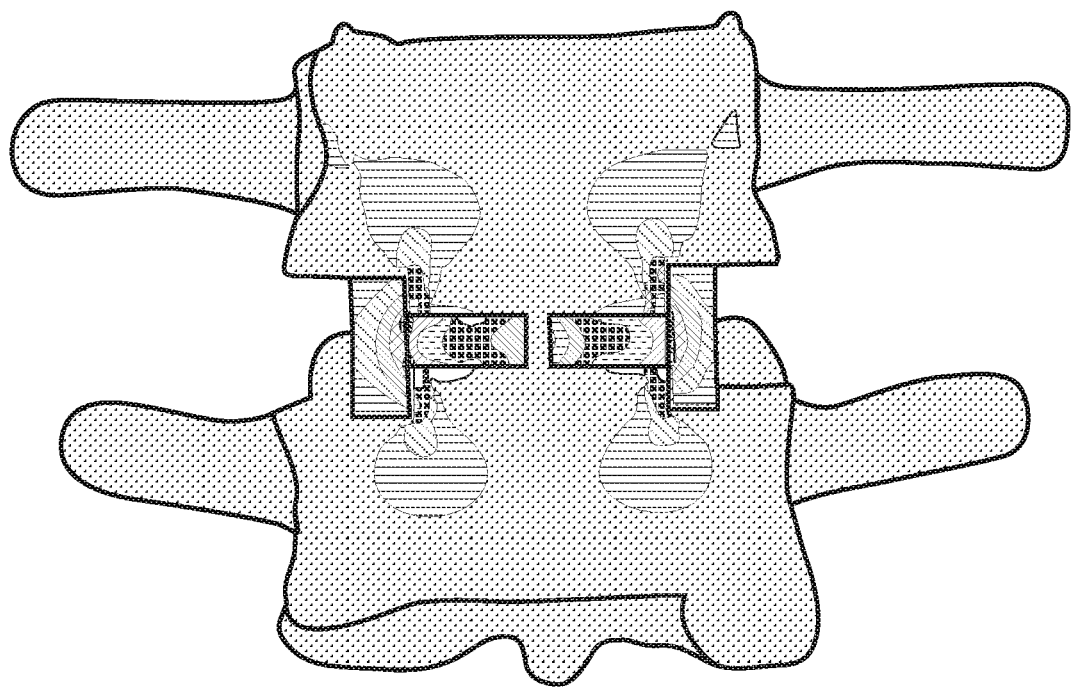
FIG. 24 shows Von Mises stress distribution on the cage itself.
Figure 24:

FIG. 24 shows Von Mises stress distribution on the cage itself demonstrating asymmetrical load distribution as well as the movement of the stresses away from the interface with the cage itself towards the interior of the vertebral body. This would have the potential benefits of decreased implant subsidence due to the distribution of forces on the vertebral body itself. This result also demonstrates that fusion within the cage itself does not rely on the cage to be directly loadbearing with the endplate and thus the cage only acts as a temporary spacer until the fusion within the device has been achieved.

Figure 25:
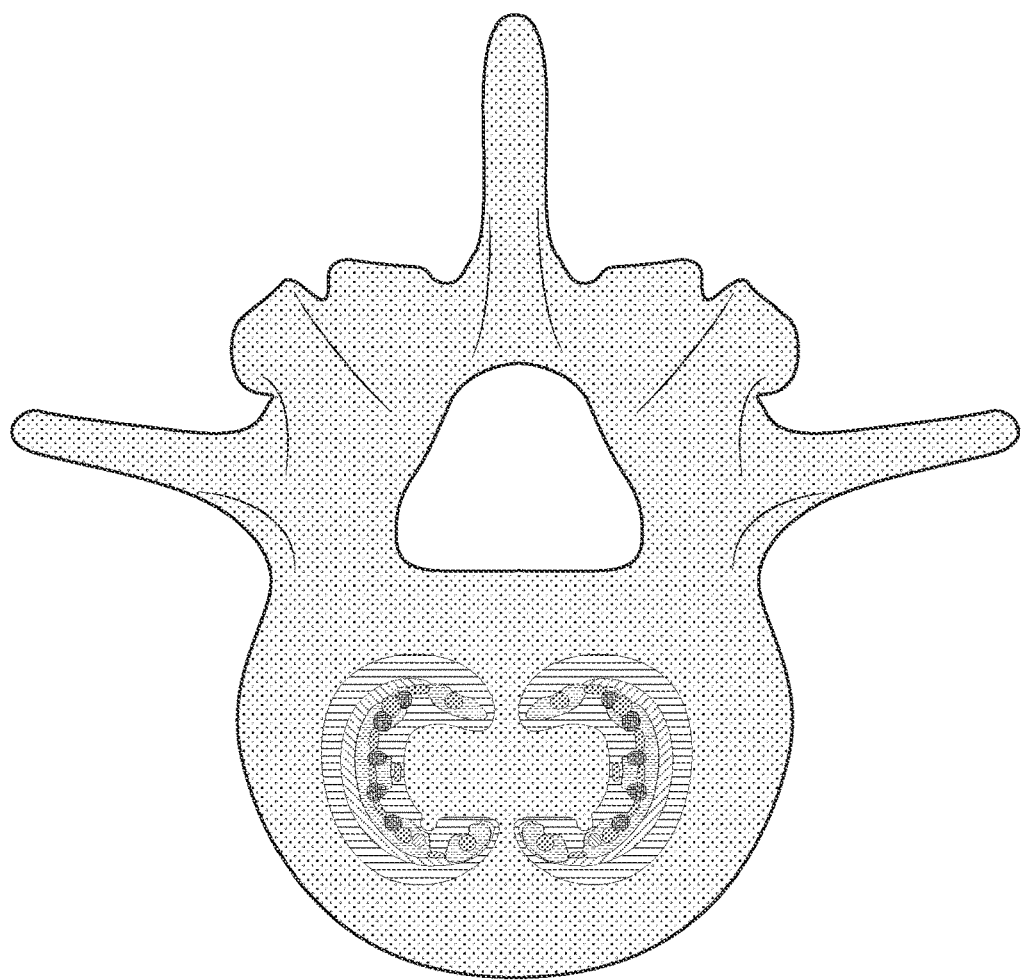
FIG. 25 shows Von Mises stress (bone and cage) on a further embodiment of the disclosure.
Figure 25:
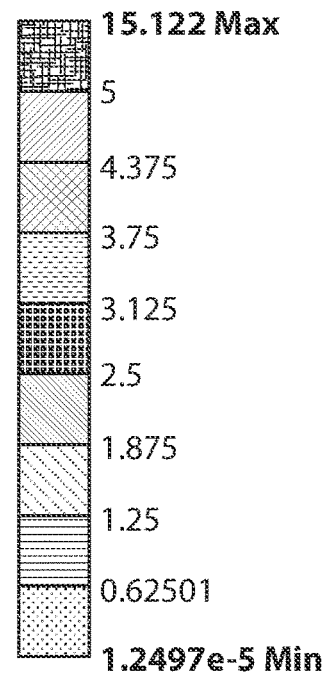

FIG. 25 shows Von Mises stress (bone and cage), demonstrating the intimate load distribution of stresses between the cage and the graft itself.

Figure 26:
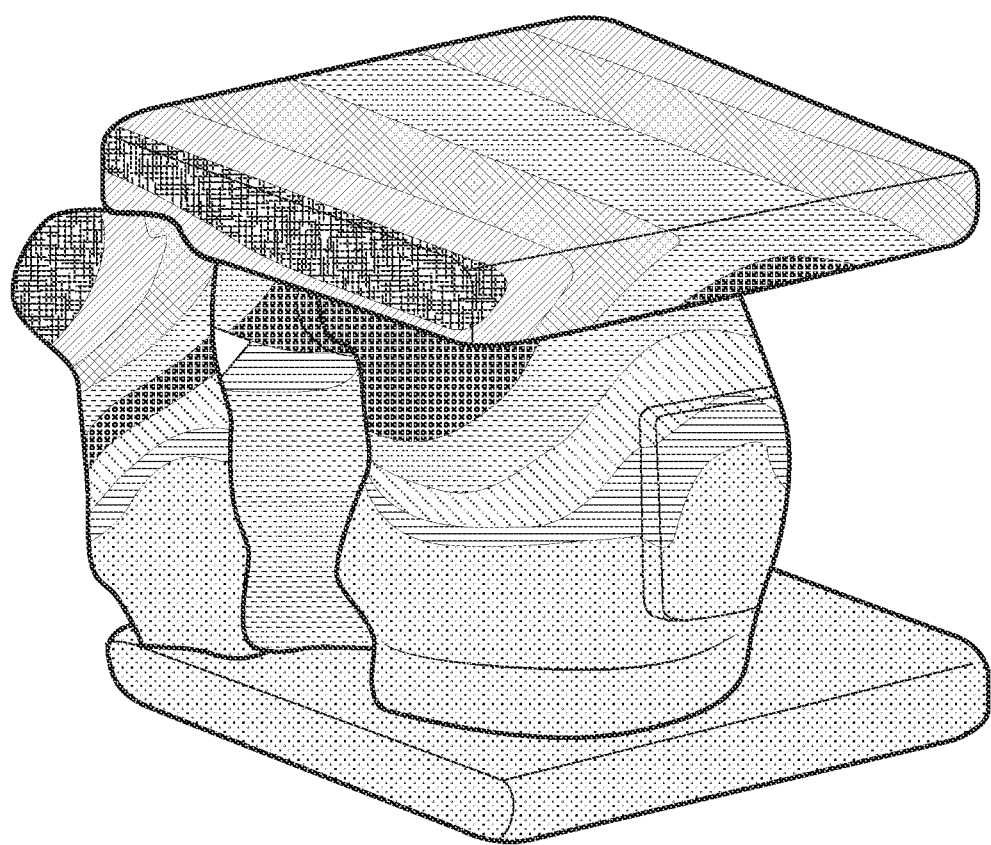
FIG. 26 shows global deflection iso view on the device of FIG. 25.
Figure 26:
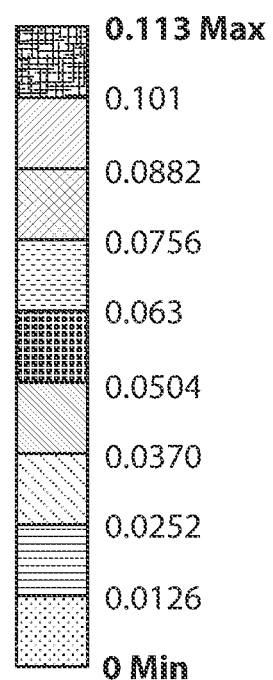

FIG. 26 shows global deflection iso view for a second embodiment, the KNOB design as shown in FIGS. 1, 2 and 7. The deflection is virtually 0 and markedly different compared to the control, non-fused case as shown standard peek cage condition.

Figure 27:
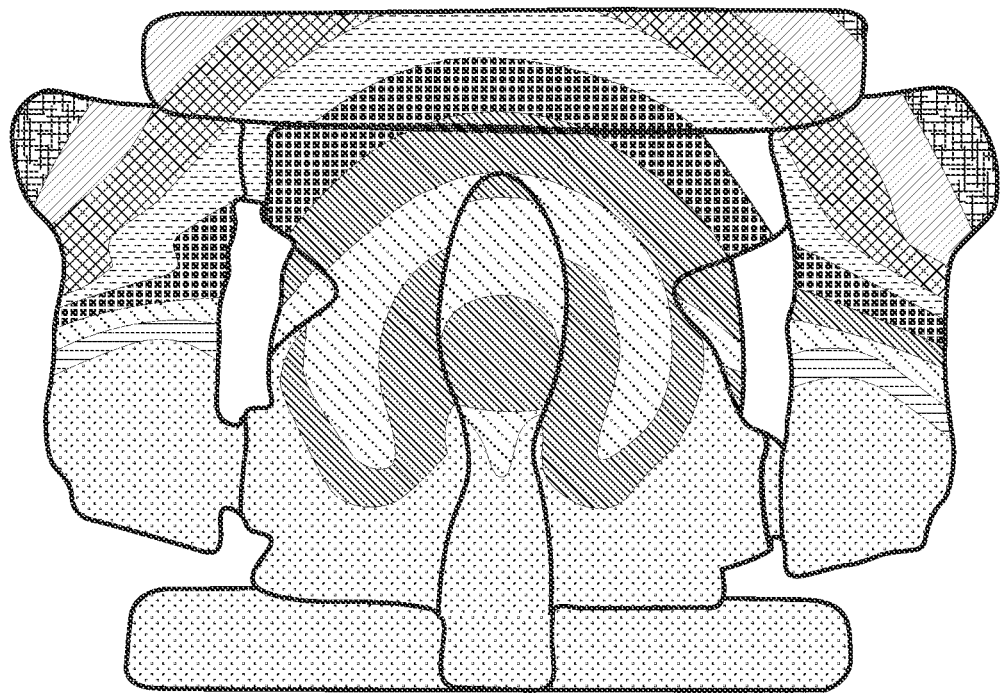
FIG. 27 shows global deflection posterior view on the device of FIG. 25.
Figure 27:
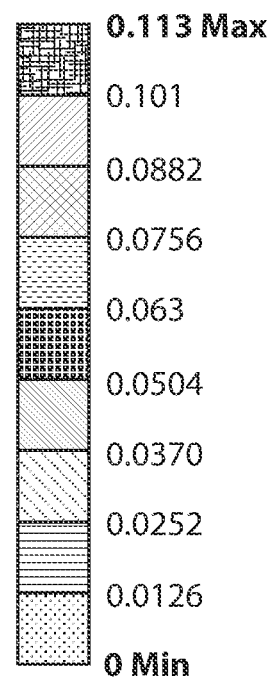
Figure 28:
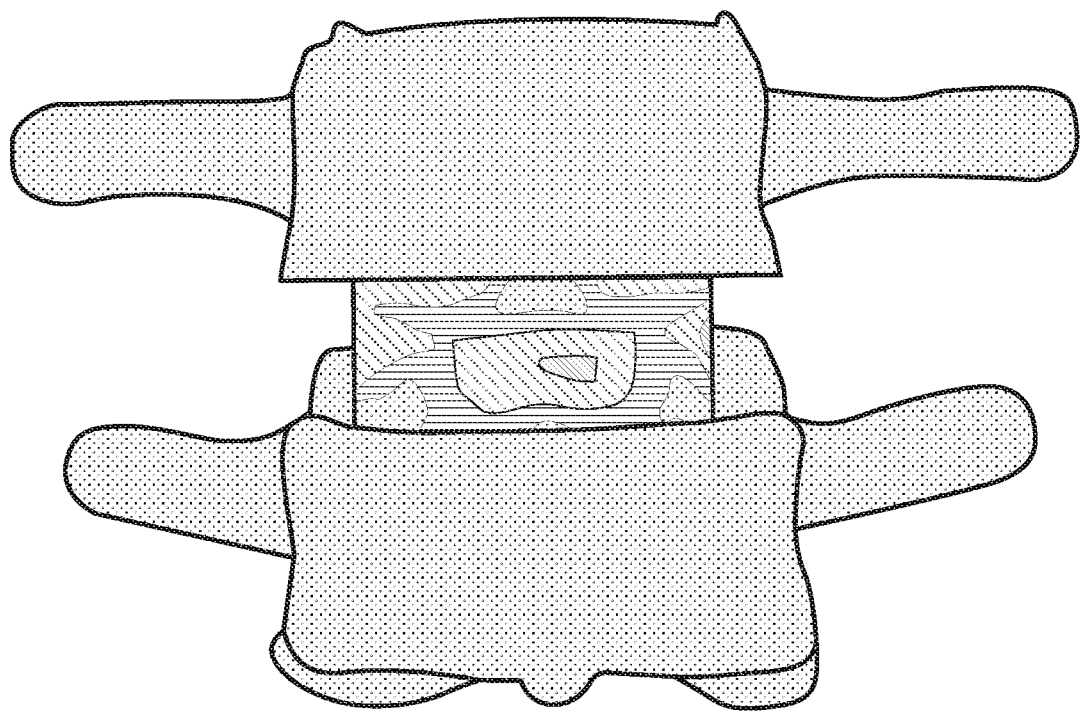
FIG. 28 shows Von Mises stress 1 and immediately demonstrates the symmetry of the loading and the lack of hotspots on the vertebral bodies themselves on the device of FIG. 25.
Figure 28:
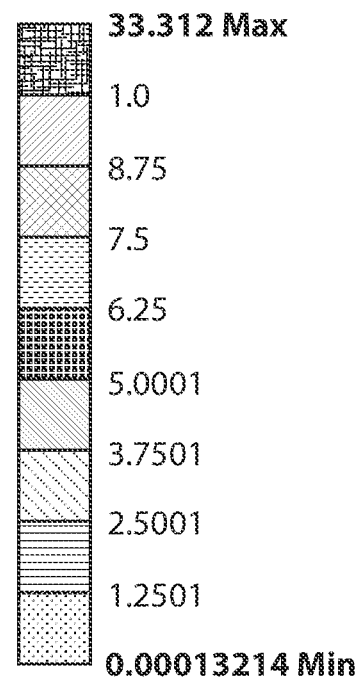

FIG. 27 shows that Global deflection posterior view is virtually 0 and markedly different compared to the control, non-fused case as shown standard peek cage in the previous case FIG. 28 shows Von Mises stress 1 and immediately demonstrates the symmetry of the loading and the lack of hotspots on the vertebral bodies themselves.

Figure 29:
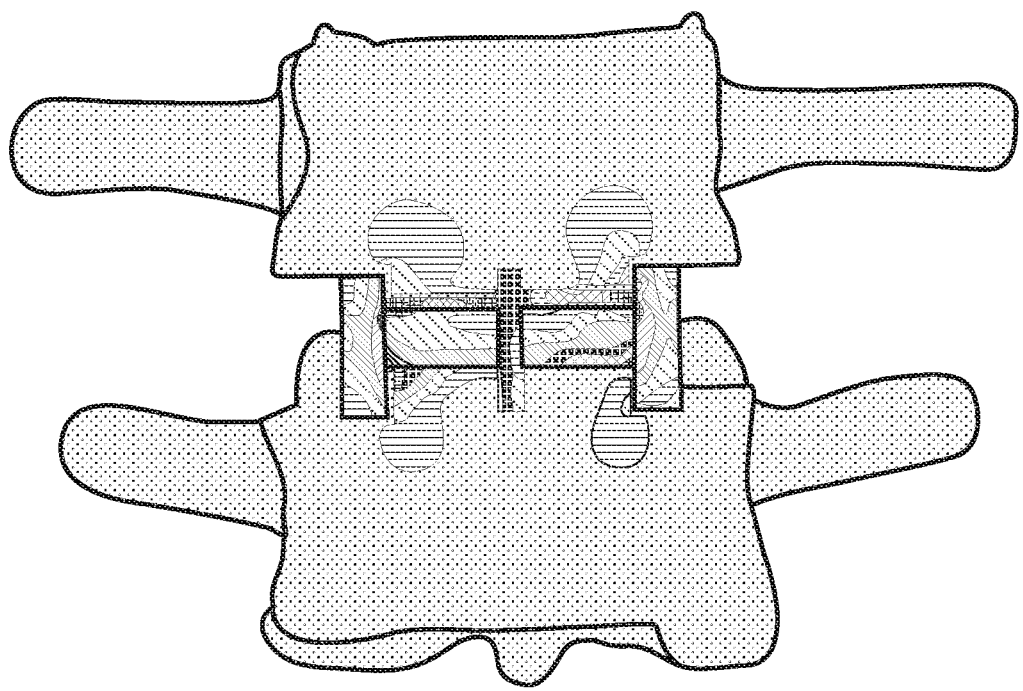
FIG. 29 shows Von Mises stress distribution on the cage itself on the device of FIG. 25.
Figure 29:
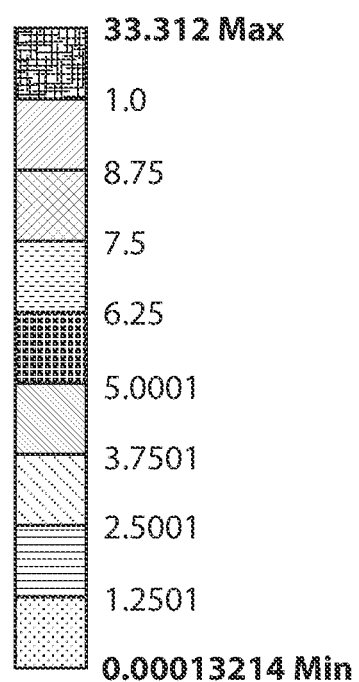

FIG. 29 shows Von Mises stress distribution on the cage itself demonstrating asymmetrical load distribution as well as the movement of the stresses away from the interface with the cage itself towards the interior of the vertebral body. This would have the potential benefits of decreased implant subsidence due to the distribution of forces on the vertebral body itself. This result also demonstrates that fusion within the cage itself does not rely on the cage to be directly loadbearing with the endplate and thus the cage only acts as a temporary spacer until the fusion within the device has been achieved. Note the maximum stress range in the current model is higher than that compared to the knob design.

Figure 30:
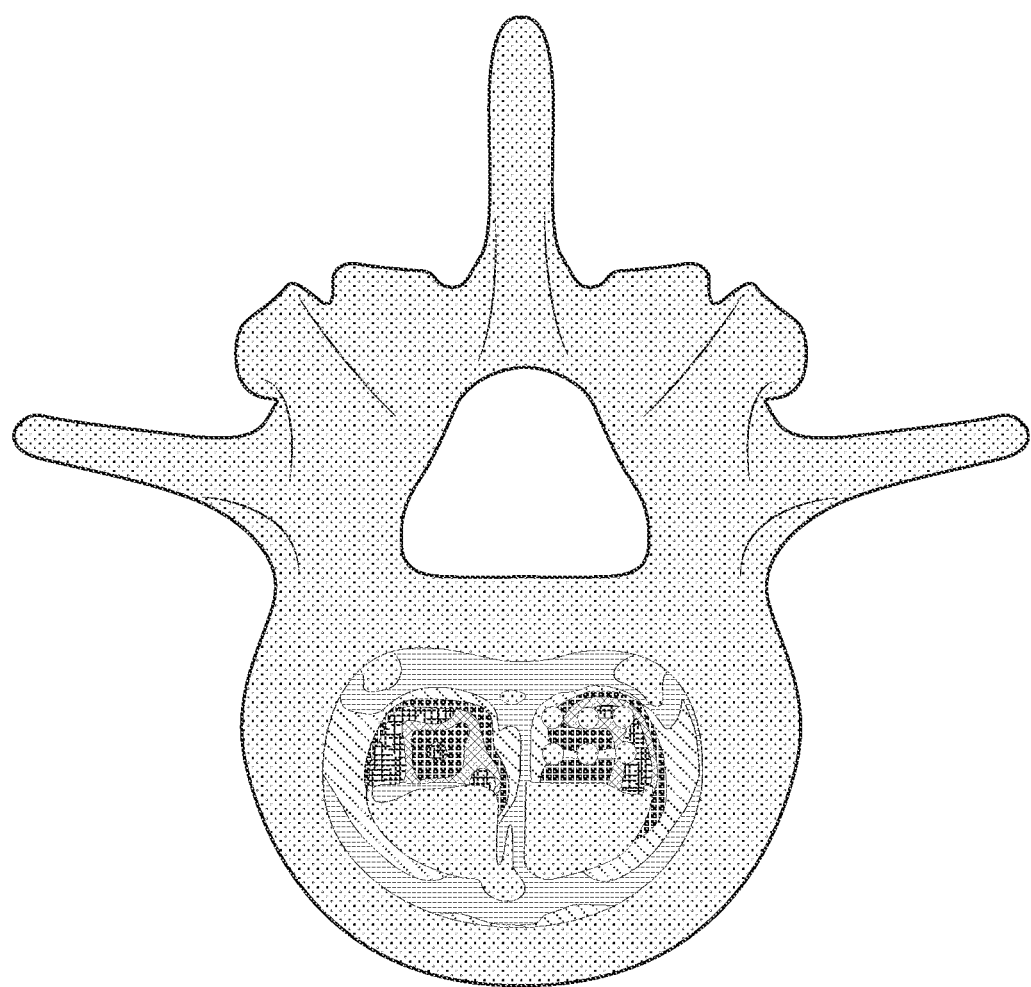
FIG. 30 shows Von Mises stress (bone and cage) on the device of FIG. 25.

FIG. 30 shows Von Mises stress (bone and cage) demonstrating the intimate load distribution of stresses between the cage and the graft itself.

Figure 31:
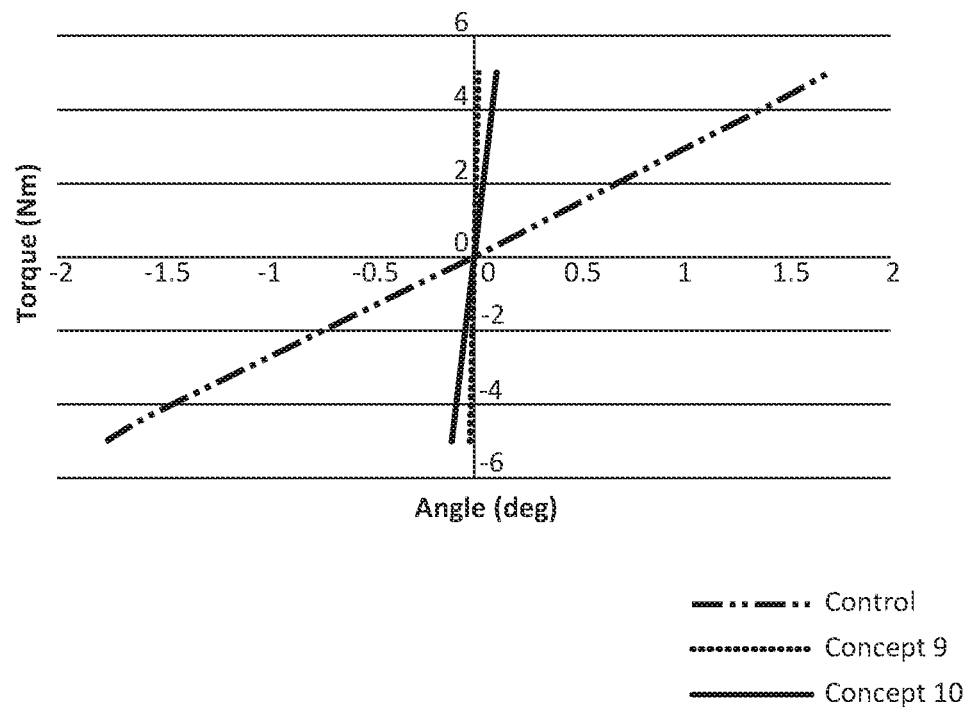
FIG. 31 shows a summary of lateral bending demonstrating applied torque vs. rotation for the control and the titanium plate device and knob device.

FIG. 31 shows a summary of lateral bending demonstrating applied torque vs. rotation, concept 9 is the titanium plate design and Concept 10 is the KNOB design This figure demonstrates the angular deformation versus torque for the control and 2 of our plate design and the knob design. As clearly demonstrated in his graph the angular deflection upon applied torque and the control is as expected as there is lack of fusion as well as lack of integration or interaction between the bone within the cage and the device itself. In contrast designs 9 and 10 demonstrate a market reduction in angular deflection upon applied torque reflecting the integration and interaction between the bone within the cage, that has yet to completely unite from one level to the next, however does participate with the device permutations itself to provide a change in the biomechanical environment. This is an unexpected finding and forms in part the novelty within our device and concepts.

While the device has been described in reference to its preferred embodiments, it is to be understood that the words which have been used are words of description rather than limitation and that changes may be made without departing from the scope of the application as defined by the appended claims.

It is to be understood that a reference herein to a prior art document does not constitute an admission that the document forms part of the common general knowledge in the art in Australia or in any other country.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the device of the disclosure.

The invention claimed is:

1. A device adapted to be positioned between two bone regions, the device comprising:
a body;
first and second device ends, the first device end configured to be positioned at or adjacent a first bone region and the second device end configured to be positioned at or adjacent a second bone region the first and second device ends including an opening facing the first and second bone regions respectively,
the body extending along a longitudinal axis between the first and second device ends;
at least one wall extending between the first device end and the second device end, the wall being defined by an outer surface and a continuous inner surface, the inner surface defining an interior cavity that extends the length of the device and extending circumferentially around the entire interior cavity, and,
a load arrangement comprising at least two load elements, a first load element positioned proximal the first device end and comprising a first planar surface extending into the interior cavity and facing the first device end and a second planar surface extending into the interior cavity and facing the second device end, and a second load element positioned proximal the second device end and comprising a third planar surface facing the first device end and a fourth planar surface facing the second device end,
the second planar surface and the third planar surface being in a facing arrangement with one another and being spaced apart in the longitudinal direction by the continuous inner surface of the wall, wherein the first load element is configured to interact with either the second load element or the wall to transmit load in more than one plane to load graft material positioned within the cavity, one plane in which load is transmitted extending between the two bone regions in line with the longitudinal axis.

2. A device as defined in claim 1, wherein the load element comprises a protrusion extending into the cavity from at least one wall the protrusion being positioned with respect to the wall such that the protrusion acts as a cantilever.

3. A device as defined in claim 1, wherein the load arrangement comprises a plurality of load elements extending into the cavity from at least one wall of the cage.

4. A device as defined in claim 3 wherein each load element has two planar faces extending substantially parallel to one another from the wall.

5. A device as defined in claim 1, wherein the load elements are deformable.

6. A device as defined in claim 1, wherein the load arrangement comprises a plurality of load elements in the form of interacting features configured to interact with one another, the interacting features being shaped to place load on material in the cavity.

7. A device as defined in claim 1, wherein the load arrangement comprises at least one load element extending into the cavity from the wall and at least one elongate member extending from the load element.

8. A device as defined in claim 7, wherein the load arrangement comprises two load elements extending into the cavity from the wall and the elongate member extends between the load elements to facilitate load between the load elements.

9. A device as defined in claim 8, wherein the load elements are positioned proximal opposing ends of the cage.

10. A device as defined in claim 9, wherein the elongate member extends longitudinally with respect to an axis extending through the cavity from one load element to the other.

11. A device as defined in claim 1 wherein the load arrangement is biased toward a centre of the cavity.

12. A device as defined in claim 1 further comprising an insertable divider to divide the cavity into a plurality of sections.

13. A device as defined in claim 1, wherein at least a portion of the load arrangement comprises of titanium.

14. A device as defined in claim 1, wherein at least a portion of the load arrangement comprises of a degradable polymer.

15. A device as defined by claim 14, wherein the degradable polymer includes an active agent which is released as the polymer degrades.

16. A device as defined in claim 1, wherein the continuous inner surface of the wall and the load elements define a load region intermediate the load elements, the load region being configured for retaining graft positioned between the load elements within the interior cavity of the device.

17. A device as defined in claim 1, wherein the continuous inner surface of the wall is non-porous.

18. A device as defined in claim 1, wherein the load elements extend part way laterally with respect to the interior cavity.

19. A device for bone integration, the device comprising:
a body;
first and second device ends, the first device end configured to be positioned at or adjacent a first bone region and the second device end configured to be positioned at or adjacent a second bone region the first and second device ends including an opening facing the first and second bone regions respectively,
the body extending along a longitudinal axis between the first and second device ends;
at least one wall extending between the first device end and the second device end, the wall being defined by an outer surface and a continuous inner surface, the inner surface defining an interior cavity that extends the length of the device and extending circumferentially around the entire interior cavity,
a first load element positioned proximal the first device end and comprising a first planar surface extending into the interior cavity and facing the first device end and a second planar surface extending into the interior cavity and facing the second device end, and a second load element positioned proximal the second device end and comprising a third planar surface facing the first device end and a fourth planar surface facing the second device end,
the second planar surface and the third planar surface being in a facing arrangement with one another and being spaced apart in the longitudinal direction by the continuous inner surface of the wall, the first load element and the second load element extending from the wall and defining a load region within the interior cavity, the load region being configured such that the load on material deposited in the load region is greater than the load on material external to the load region.

20. A device adapted to be positioned between two bone regions, the device comprising:
a body; first and second device ends, the first device end configured to be positioned at or adjacent a first bone region and the second device end configured to be positioned at or adjacent a second bone region the first and second device ends including an opening facing the first and second bone regions respectively,
the body extending along a longitudinal axis between the first and second device ends;
at least one wall defined by an outer surface and a continuous inner surface extending between the first device end and the second device end, the wall defining at least one interior cavity extending the length of the device, and,
a load arrangement comprising at least two load elements, a first load element positioned proximal the first device end and comprising a first planar surface extending into the interior cavity and facing the first device end and a second planar surface extending into the interior cavity and facing the second device end, and a second load element positioned proximal the second device end and comprising a third planar surface facing the first device end and a fourth planar surface facing the second device end, the second planar surface and the third planar surface being in a facing arrangement with one another and being spaced apart in the longitudinal direction by the continuous inner surface of the wall which extends circumferentially around the entire interior cavity and wherein the first load element is configured to interact with either the second load element or the wall to transmit load to graft material positioned within the cavity, at least a portion of the load comprising torsional load.

21. A device adapted to be positioned between two bone regions, the device comprising:
a body;
first and second device ends, the first device end configured to be positioned at or adjacent a first bone region and the second device end configured to be positioned at or adjacent a second bone region the first and second device ends including an opening facing the first and second bone regions respectively,
the body extending along a longitudinal axis between the first and second device ends;
at least one wall defined by an outer surface and a continuous inner surface extending between the first device end and the second device end, the wall defining at least one interior cavity extending the length of the device, and,
a load arrangement extending into the interior cavity and comprising at least two load elements, a first load element positioned proximal the first device end and comprising a first planar surface extending into the interior cavity and facing the first device end and a second planar surface extending into the interior cavity and facing the second device end, and a second load element positioned proximal the second device end and comprising a third planar surface facing the first device end and a fourth planar surface facing the second device end, the second planar surface and the third planar surface being in a facing arrangement with one another and being spaced apart in the longitudinal direction by the continuous inner surface of the wall which extends circumferentially around the entire interior cavity and, the load elements being sufficiently large to interact with graft located within the interior cavity in more than one plane,
the first load element configured to interact with either the second load element or the wall to transmit load to graft material positioned within the cavity.

22. A device as defined in claim 21, wherein the device transmits load including lateral bending, axial rotation and flexion extension between the user of the device and the device.

23. A method of promoting stability in bone comprising:
positioning a device as defined in claim 1 between two bone regions; and
placing graft material within the cavity of the device such that the load arrangement places load on the graft material within the cavity.

* * * * *